(12) United States Patent
Le Cocq et al.

(10) Patent No.: US 7,881,876 B2
(45) Date of Patent: Feb. 1, 2011

(54) METHODS AND SYSTEMS FOR REMOVING OFFSET BIAS IN CHEMICAL ARRAY DATA

(75) Inventors: Christian A. Le Cocq, Mountain View, CA (US); Glenda C. Delenstarr, Redwood, CA (US); John F. Corson, Mountain View, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 943 days.

(21) Appl. No.: 11/580,744

(22) Filed: Oct. 12, 2006

(65) Prior Publication Data

US 2008/0090735 A1    Apr. 17, 2008

(51) Int. Cl.
    *G06F 7/00*    (2006.01)
(52) U.S. Cl. .................... 702/19; 702/20; 703/11; 703/12; 435/6
(58) Field of Classification Search .................... None
    See application file for complete search history.

(56) References Cited

U.S. PATENT DOCUMENTS

| | | |
|---|---|---|
| 6,171,797 B1 | 1/2001 | Perbost |
| 6,180,351 B1 | 1/2001 | Cattell |
| 6,221,583 B1 | 4/2001 | Kayyem et al. |
| 6,222,664 B1 | 4/2001 | Dorsel et al. |
| 6,232,072 B1 | 5/2001 | Fisher |
| 6,242,266 B1 | 6/2001 | Schleifer et al. |
| 6,251,685 B1 | 6/2001 | Dorsel et al. |
| 6,320,196 B1 | 11/2001 | Dorsel et al. |
| 6,323,043 B1 | 11/2001 | Caren et al. |
| 6,345,115 B1 * | 2/2002 | Ramm et al. ............ 382/133 |
| 6,355,921 B1 | 3/2002 | Staton et al. |
| 6,371,370 B2 | 4/2002 | Sadler et al. |
| 6,406,849 B1 | 6/2002 | Dorsel et al. |
| 6,410,243 B1 | 6/2002 | Wyrick et al. |
| 6,486,457 B1 | 11/2002 | Dorsel et al. |
| 6,518,556 B2 | 2/2003 | Staton et al. |

FOREIGN PATENT DOCUMENTS

WO    WO 93/18186    9/1993

OTHER PUBLICATIONS

Jianping Hua, et al., "Normalization Benefits Microarray-Based Classification," EURASIP Journal on Bioinformatics and Systems Biology, vol. 2006, Article ID 43056, 13 pages, 2006. doi:10.1155/BSB/2006/43056.*
Dodd et al. ( Bioinformatics (Oxford, England), (Nov. 1, 2004) vol. 20, No. 16, pp. 2685-2693. Electronic Publication: May 14, 2004.*
Bengtsson, Henrik et al.; BMC bioinformatics, (Nov. 12, 2004) vol. 5, pp. 177. Electronic Publication: Nov. 12, 2004.*
Colantuoni et al., SNOMAD (Standardization and NOrmalization of Microarray Data): web-accessible gene expression data analysis. vol. 18 No. Nov. 2002, pp. 1540-1541.
Parmigiani et al., The Analysis of Gene Expression Data, Springer-Verlag New York, Inc. 2003, pp. 210-229.
www.netlib.org/a/Loess, pp. 1-46, downloaded Jun. 28, 2006.
Cleveland et al., Locally Weighted Regression: An Approach to Regression Analysis by Local Fitting, Journal of the American Statistical Association, vol. 83, Sep. 1988,pp. 596-610.).
Cleveland., Pobust Loccally Weighted Regression and Smoothing Scatterplots. Journal of the American Statistical Association, vol. 74, No. 368, Dec. 1979, pp. 829-836.

* cited by examiner

*Primary Examiner*—Mary K Zeman

(57) ABSTRACT

Methods, systems and computer readable media for quantifying and removing offset bias signals in a chemical array data set having one or more channels. In one embodiment, for each channel of data in the data set, a first set of features is selected from the data set. Surface intensities are calculated for features in the first selected set of features and surface intensifies of features not in the first selected set are calculated from the calculated surface intensities. A second set of features is selected, the intensity values of which are within a range of correspondingly located surface intensity values defined by upper and lower threshold intensities. Secondary surface intensifies are calculated for features in the second selected set of features and secondary surface intensities for all other locations on the array that were not locations corresponding to the features having secondary surface intensities calculated therefore, are calculated. Feature intensities of the channel features are then corrected as a function of the secondary surface intensities.

22 Claims, 17 Drawing Sheets

METHODS AND SYSTEMS FOR REMOVING OFFSET BIAS IN CHEMICAL ARRAY DATA

BACKGROUND OF THE INVENTION

Researchers use experimental data obtained from chemical arrays such as microarrays and other similar research test equipment to cure diseases, develop medical treatments, understand biological phenomena, and perform other tasks relating to the analysis of such data. However, the conversion of useful results from this raw data is restricted by physical limitations of, e.g., the nature of the tests and the testing equipment. All biological measurement systems leave their fingerprint on the data they measure, distorting the content of the data, and thereby influencing the results of the desired analysis. Further, the systems for manufacturing and processing the arrays may also induce systematic error.

Sources of background signal can inflate the signal intensities associated with certain of the features on an array. The background signal of an array may contribute systematic feature-position-related background intensity to the measured intensity data read from the array and may cause inaccurate determination of intensity levels and the gene expression levels or other measurements corresponding thereto, during analysis. For example, systematic biases can distort microarray analysis results and thus conceal important biological effects sought by the researchers. Biased data can cause a variety of analysis problems, including signal compression, aberrant graphs, and significant distortions in estimates of differential expression. Types of systematic biases include gradient effects, differences in signal response between channels (e.g., for a two channel system), variations in hybridization or sample preparation, pen shifts and subarray variation, and differences in RNA inputs.

Gradient effects or "trends" are those in which there is a pattern of expression signal intensity which corresponds with specific physical locations on the substrate of the array and which may typically be characterized by a smooth change in the expression values from one location on the array to another. This can be caused by variations in array design, manufacturing, and/or hybridization procedures. FIG. 1 shows an example of distortion caused by gradient effects, i.e., a trend, where it can be observed that the signal intensity shows a gradually increasing pattern moving from a first edge 100 (see signals corresponding at 200) to a second edge 102 (corresponding signals 202) of the array. An additive trend is formed when the signal values are added to the amount of true signal level of the feature. A multiplicative trend is formed when the trend is a multiple of the true signal level, so that noise is somewhat proportional to the signal level of the feature. Another example of a gradient effect is a hybridization dome or "hyb dome", which is a gradient or trend thought to occur from hybridization processing, where the signal around the perimeter of the array is significantly less than in the middle of the array, because of the impact of the bubbler that circulates the target during hybridization.

Detrending of array data is important not only for validating the data values within an array and for comparison of values within the array (intraarray comparisons), but also for valid comparison of data values between different array (interarray comparisons)

Efforts at spatially detrending array data have been made based on statistical processing of log ratio values (signal ratios between first and second channels of a scanner reading the same array, or between two single channel readings from two arrays) or on statistical processing of the signal values themselves. The latter is more difficult since signals may vary over many orders of magnitude and skew the results for some statistical approaches. By working with log ratios between signals, these values vary less and should be centered around a zero ratio value, making it much easier to apply statistical techniques to the data in a reliable fashion.

One such effort was made using a publicly available software package referred to as SNOMAD (Standardization and Normalization of Microarray Data), see Colantuoni et al., "SNOMAD (Standardization and Normalization of MicroArray Data): web-accessible gene expression data analysis", Bioinformatics Applications Note, Vo. 18, no. 11, 2002, pp 1540-1541. SNOMAD provides scripts in the R statistical language (www.r-project.org) that are used to generate Z-scores for normalization of variance in the gene expression values of a microarray. In order to correct for variance in gene expression ratios (y-axis) that is unequal across the range of gene expression levels (x-axis), each local mean adjusted log expression ratio (y-value) is standardized to the estimation of the standard deviation of log ratio observations that share similar mean expression levels, as identified by being proximal on the x-axis, as defined by a "span" parameter. This results in the generation of Z-scores in locally estimated standard deviation units, see Parimigiani et al., *The Analysis of Gene Expression Data*, Springer-Verlag New York, Inc. 2003, pp. 210-217. A robust local regression ("loess") is used to calculate the local mean gene expression ratio as it varies across the range of gene expression intensity. The calculation of local mean ratios may not be effective for certain types of trends where signal values vary depending upon the location of a feature on the array (e.g., as in the case of a hyb dome, or other spatially related trends). Further, the scripts provided in SNOMAD are not easily integratable into other analysis software packages, such as feature extraction packages, and are therefore not helpful for automating feature extraction processes.

Other efforts at removing systematic bias from a chemical array data set to effect spatial detrending involve collecting the feature signals as a subset of all feature signals on a chemical array, for each channel of the chemical array data set, wherein the intensities of the feature signals in the subset are each close to zero. These feature signals are then fit to an empirical model and the model is used to predict the local offset value for each feature signal on the array, wherein the local offset value corresponds to a feature with a zero level of biological signal. Thus, by removing the local offset value from each feature signal (which may vary depending upon the location of the particular feature on the array), the resultant offset-subtracted feature signals are intended to be true measurements of the chemical or biological entity that the features are designed to measure. This approach typically uses a predetermined percentage of the signals at the lowest end of the intensity range to fit to the empirical model. As one example, the lowest 1% of the feature signal intensities are typically used. A problem with this approach is that the values of the lowest predetermined percentage of the signals varies depending upon the makeup of the features on the array and upon the sample that was hybridized to the array, from which the signals are read. For example, referring to FIG. 2, three histograms 202, 204 and 206 are plotted to represent the signal data from three hypothetical chemical arrays all having the same number of features. The intensities of the feature signals are plotted on the horizontal axis and intensity increases moving rightward. The number of features corresponding to the intensities of the signals therefrom are plotted along the vertical axis and increase in the upward direction.

In the first plot 202, the number of features having relatively low intensities is a smaller percentage of the overall number of features than is the case with the second plot 204. Further, the plot 206 show that almost all features have very low or no signal, as the high intensity portion of the plot is very near or at zero number of features in this region. Using the above approach, if a fixed percentage of the lowest intensity signals is selected from each plot, for example, the lowest 1% of signal intensities, the selection for plot 202 includes intensities up to intensity value 212, whereas the selection for plot 204 includes intensities only up to intensity value 214, and the selection for plot 206 includes intensities only up to intensity value 216. Thus, it can be seen that the greater the relative overall percentage of relatively low intensity feature signals on the array, the lower is the estimate of the zero value for the signal data (correction for offset). Thus, this approach may have a tendency to overestimate or underestimate the offset (background noise) depending upon the makeup of the array being analyzed.

Put another way, if all of the signals in a lower peak such as the lower peak shown in plot 202, 204 or 206, for example, are signals with zero biological signal (i.e., signal from sample bound to a probe), then they are distributed in a Gaussian distribution about a peak value. The signals in the distribution are not all at the same value and thus form the Gaussian distribution because of the random, non-spatial noise introduced by the measurement system that measure that signals, thereby adding uncertainty to these signals. Ideally, a background subtraction method would find "zero" signal level to be the center of the Gaussian peak. Because the Gaussian peak has a bell shape and a width, if the background subtraction method selects the dimmest or lowest 1% of the signals on the array, the more probes that are in the Gaussian distribution, the further down to the left tail of that lower peak distribution selection base on the lowest 1% ends up. Thus, the further left that this selection results in, the further away it moves from the true "zero" level, as the signal level decreases as you move leftward along the left tail of the distribution. Therefore, FIG. 2 illustrates that using the dimmest 1% of signals to estimate background noise, assuming a finite background noise, the zero signal level will be estimated at different levels depending upon the percentage of the signals that are contained in the group of data centered around the signal seen for features with no true biological signal.

In view of the existence of offset biases such as background signals, experimentalist, designers, and manufacturers of chemical arrays and chemical array data processing systems have recognized a need for a reliable and efficient methods and systems for quantifying and removing systematic feature-position-related offset biases within a chemical array data set.

SUMMARY OF THE INVENTION

Methods, systems and computer readable media for quantifying and removing offset bias signals in a chemical array data set having one or more channels. For each channel of data in the data set, a first set of features is selected from the data set; surface intensities are calculated for each feature in the first selected set of features; a spread of the intensity values of the selected set of features is calculated from the calculated surface intensities; a second set of features is selected, the intensity values of which are within a range of intensity values between ± spread times a predetermined multiplier; surface intensities are calculated for features in the second selected set of features; surface intensities for all other features in the data set are calculated for the channel from the calculated surface intensities for each feature in the second selected set; feature intensities of the channel features are corrected by subtracting surface intensities at locations that correspond to respective locations of the feature intensities; and the corrected feature intensities are outputted.

In at least one embodiment, the selected features in the first set are negative control features.

In at least one embodiment, the second set includes the first set

In at least one embodiment, the surface intensities are calculated for all features in the second selected set.

In at least one embodiment, the second selected set of features is sampled, wherein the calculation of surface intensities is performed on a sampled, subset of the second selected set that is smaller than the second selected set.

In at least one embodiment, the sampling is performed with a moving window filter.

In at least one embodiment, a predetermined percentage of features from the second selected set of features is randomly selected, wherein the calculation of the surface intensities is performed on the signal intensities of the randomly selected features, and wherein the predetermined percentage is less than one hundred percent.

In at least one embodiment, at least one of the selecting steps further includes excluding features having non-uniform intensity distributions.

In at least one embodiment, the calculation of surface intensities for each feature in the first selected set of features comprises calculating a surface fit to intensity values of the features with a polynomial approximation algorithm.

In at least one embodiment, the polynomial approximation algorithm is a second-order polynomial approximation algorithm.

In at least one embodiment, the calculation of surface intensities for each feature in the first selected set of features comprises locally-weighted, least-squares regression.

In at least one embodiment, the calculation of surface intensities for features in the second selected set of features comprises locally-weighted, least-squares regression.

In at least one embodiment, the calculation of surface intensities for features in the second selected set of features comprises calculating a surface fit to intensity values of the features with a polynomial approximation algorithm.

In at least one embodiment, the polynomial approximation algorithm is a second-order polynomial approximation algorithm.

Methods, systems and computer readable media are provided for quantifying and removing offset bias signals in a chemical array data set having one or more channels, wherein, for each channel of data in the data set, a first set of features is selected from the data set; surface intensities for features in the first selected set of features are calculated and surface intensities of features not in the first selected set are calculated from the calculated surface intensities; a second set of features are selected, the intensity values of which are within a range of correspondingly located surface intensity values defined by upper and lower threshold intensities; secondary surface intensities are calculated for features in the second selected set of features and secondary surface intensities are calculated for all other locations on the array that were not locations corresponding to the features having secondary surface intensities calculated therefore; feature intensities of the channel features are corrected as a function of the secondary surface intensities; and the corrected feature intensities are outputted.

In at least one embodiment, the upper and lower threshold intensities are calculated as a function of the calculated surface intensities.

In at least one embodiment, the function of the calculated surface intensities includes calculation of a spread of the intensity values of the selected set of features from the calculated surface intensities.

In at least one embodiment, the spread is calculated by a robust technique, excluding outliers of the intensity values.

In at least one embodiment, the correction of feature intensities comprises subtracting secondary surface intensities at locations that correspond to respective locations of the feature intensities.

A representation of the corrected feature intensities produced by the methods described herein is provided, that is maintained for subsequent analysis by one of: storing the representation in a computer readable medium; and transferring the representation to an intercommunicating entity via electronic signals.

A system for quantifying and removing offset bias signals in a chemical array data set having one or more channels is provided, including: at least one computer processor; an interface through which one or more chemical array data sets are received by the system; and a program, stored in one or more memory components and executed by at least one computer processor that, for each channel, selects a first set of features from the data set; calculates surface intensities for feature in the first selected set of features and calculates surface intensities of features not in the first selected set, from the calculated surface intensities; selects a second set of features the intensity values of which are within a range of correspondingly located surface intensity values defined by upper and lower threshold intensities; calculates secondary surface intensities for features in the second selected set of features and calculates secondary surface intensities for all other locations on the array that were not locations corresponding to the features having secondary surface intensities calculated therefore; and corrects feature intensities of the channel features as a function of said secondary surface intensities.

These and other features of the invention will become apparent to those persons skilled in the art upon reading the details of the methods, systems and computer readable media as more fully described below.

DETAILED DESCRIPTION OF THE INVENTION

Figure 1:
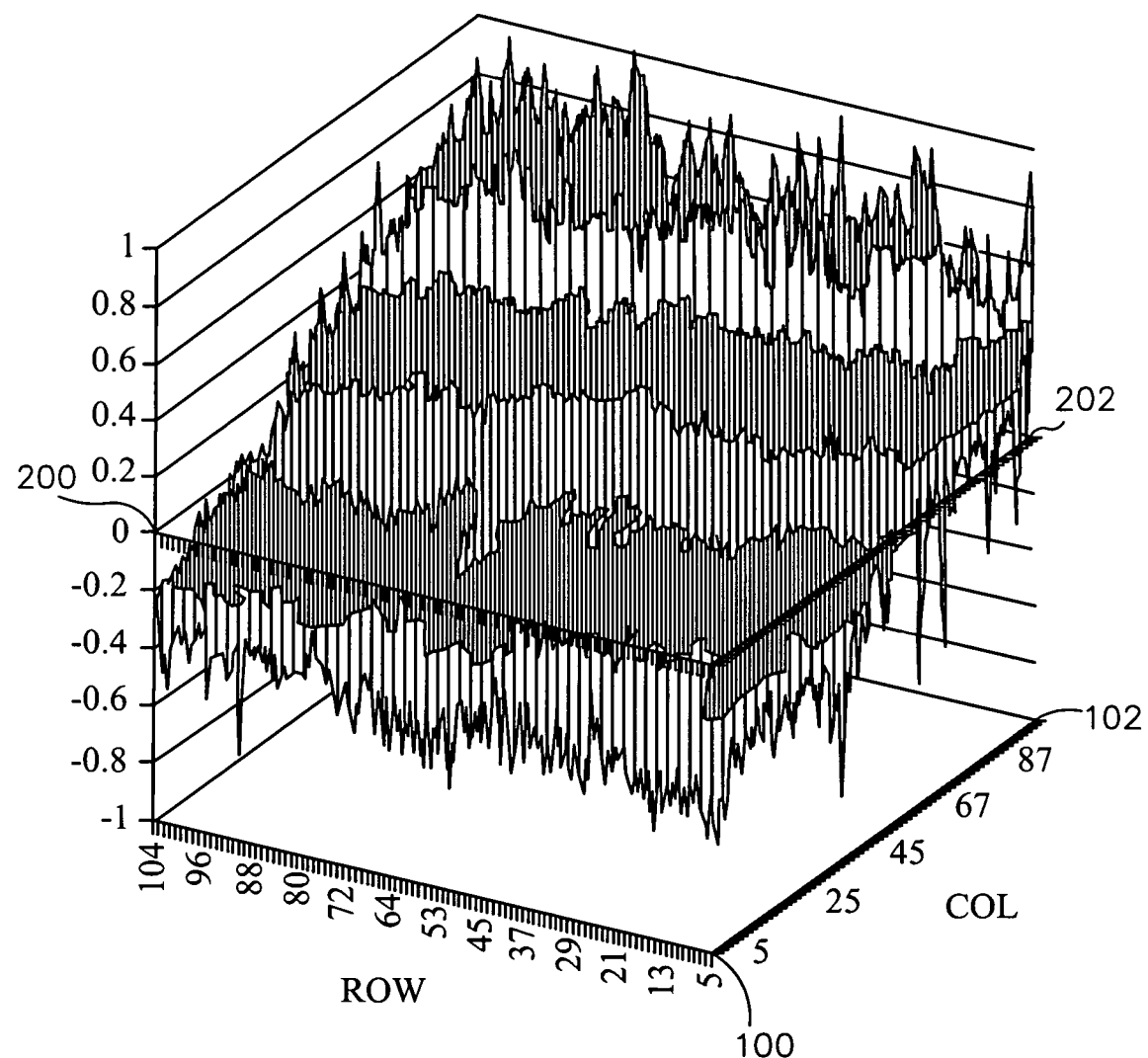
FIG. 1 shows an example of distortion caused by gradient effects, i.e., a trend.

Before the present methods, systems and computer readable media are described, it is to be understood that this invention is not limited to particular embodiments or examples described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a signal" includes a plurality of such signals and reference to "the channel" includes reference to one or more channels and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions and Further Information About Arrays

A chemical "array", unless a contrary intention appears, includes any one, two or three-dimensional arrangement of addressable regions bearing a particular chemical moiety or moieties (for example, biopolymers such as polynucleotide sequences, or other biological targets such as proteins) associated with that region, where the chemical moiety or moieties are immobilized on the surface in that region. Thus, an array may have probes that include protein and/or targets that include protein. By "immobilized" is meant that the moiety or moieties are stably associated with the substrate surface in the region, such that they do not separate from the region under conditions of using the array, e.g., hybridization and washing and stripping conditions. As is known in the art, the moiety or moieties may be covalently or non-covalently bound to the surface in the region. For example, each region may extend into a third dimension in the case where the substrate is porous while not having any substantial third dimension measurement (thickness) in the case where the substrate is non-porous. An array may contain more than ten, more than one hundred, more than one thousand more than ten thousand features, or even more than one hundred thousand features, in an area of less than 20 cm$^2$ or even less than 10 cm$^2$. For example, features may have widths (that is, diameter, for a round spot) in the range of from about 0.1 µm to about 1.0 cm. In other embodiments each feature may have a width in the range of about 1.0 µm to about 1.0 mm, such as from about 5.0 µm to about 500 µm, and including from about 10 µm to about 200 µm. Non-round features may have area ranges equivalent to that of circular features with the foregoing width (diameter) ranges. A given feature is made up of chemical moieties, (e.g., nucleic acids, proteins, etc., that bind to (e.g., hybridize to) the same target (e.g., target nucleic acid, target protein), such that a given feature corresponds to a particular target. At least some, or all, of the features are of different compositions (for example, when any repeats of each feature composition are excluded the remaining features may account for at least 5%, 10%, or 20% of the total number of features). Interfeature areas will typically (but not essentially) be present which do not carry any polynucleotide. Such interfeature areas typically will be present where the arrays are formed by processes involving drop deposition of reagents but may not be present when, for example, light directed synthesis fabrication processes are used. It will be appreciated though, that the interfeature areas, when present, could be of various sizes and configurations. An array is "addressable" in that it has multiple regions (sometimes referenced as "features" or "spots" of the array) of different moieties (for example, different polynucleotide sequences) such that a region at a particular predetermined location (an "address") on the array will detect a particular target or class of targets (although a feature may incidentally detect non-targets of that feature). The target for which each feature is specific is, in representative embodiments, known. An array feature is generally homogenous in composition and concentration and the features may be separated by intervening spaces (although arrays without such separation can be fabricated).

In the case of an array, the "target" will be referenced as a moiety in a mobile phase (typically fluid), to be detected by probes ("target probes") which are bound to the substrate at the various regions. However, either of the "target" or "target probes" may be the one which is to be detected by the other (thus, either one could be an unknown mixture of polynucleotides to be detected by binding with the other). "Addressable sets of probes" and analogous terms refer to the multiple regions of different moieties supported by or intended to be supported by the array surface.

The term "sample" as used herein relates to a material or mixture of materials, containing one or more components of interest. Samples include, but are not limited to, samples obtained from an organism or from the environment (e.g., a soil sample, water sample, etc.) and may be directly obtained from a source (e.g., such as a biopsy or from a tumor) or indirectly obtained e.g., after culturing and/or one or more processing steps. In one embodiment, samples are a complex mixture of molecules, e.g., comprising at least about 50 different molecules, at least about 100 different molecules, at least about 200 different molecules, at least about 500 different molecules, at least about 1000 different molecules, at least about 5000 different molecules, at least about 10,000 molecules, etc.

The term "genome" refers to all nucleic acid sequences (coding and non-coding) and elements present in any virus, single cell (prokaryote and eukaryote) or each cell type in a metazoan organism. The term genome also applies to any naturally occurring or induced variation of these sequences that may be present in a mutant or disease variant of any virus or cell type. These sequences include, but are not limited to, those involved in the maintenance, replication, segregation, and higher order structures (e.g. folding and compaction of DNA in chromatin and chromosomes), or other functions, if any, of the nucleic acids as well as all the coding regions and their corresponding regulatory elements needed to produce and maintain each particle, cell or cell type in a given organism.

For example, the human genome consists of approximately $3.0 \times 10^9$ base pairs of DNA organized into distinct chromosomes. The genome of a normal diploid somatic human cell consists of 22 pairs of autosomes (chromosomes 1 to 22) and either chromosomes X and Y (males) or a pair of chromosome Xs (female) for a total of 46 chromosomes. A genome of a cancer cell may contain variable numbers of each chromosome in addition to deletions, rearrangements and amplification of any subchromosomal region or DNA sequence. In certain aspects, a "genome" refers to nuclear nucleic acids, excluding mitochondrial nucleic acids; however, in other aspects, the term does not exclude mitochondrial nucleic acids. In still other aspects, the "mitochondrial genome" is used to refer specifically to nucleic acids found in mitochondrial fractions.

By "genomic source" is meant the initial nucleic acids that are used as the original nucleic acid source from which the probe nucleic acids are produced, e.g., as a template in the nucleic acid amplification and/or labeling protocols.

If a surface-bound polynucleotide or probe "corresponds to" a chromosomal region, the polynucleotide usually contains a sequence of nucleic acids that is unique to that chromosomal region. Accordingly, a surface-bound polynucleotide that corresponds to a particular chromosomal region usually specifically hybridizes to a labeled nucleic acid made from that chromosomal region, relative to labeled nucleic acids made from other chromosomal regions.

An "array layout" or "array characteristics", refers to one or more physical, chemical or biological characteristics of the array, such as positioning of some or all the features within the array and on a substrate, one or more feature dimensions, or some indication of an identity or function (for example, chemical or biological) of a moiety at a given location, or how the array should be handled (for example, conditions under which the array is exposed to a sample, or array reading specifications or controls following sample exposure).

The phrase "oligonucleotide bound to a surface of a solid support" or "probe bound to a solid support" or a "target bound to a solid support" refers to an oligonucleotide or mimetic thereof, e.g., PNA, LNA or UNA molecule that is immobilized on a surface of a solid substrate, where the substrate can have a variety of configurations, e.g., a sheet, bead, particle, slide, wafer, web, fiber, tube, capillary, microfluidic channel or reservoir, or other structure. In certain embodiments, the collections of oligonucleotide elements employed herein are present on a surface of the same planar support, e.g., in the form of an array. It should be understood that the terms "probe" and "target" are relative terms and that a molecule considered as a probe in certain assays may function as a target in other assays.

As used herein, a "test nucleic acid sample" or "test nucleic acids" refer to nucleic acids comprising sequences whose quantity or degree of representation (e.g., copy number) or sequence identity is being assayed. Similarly, "test genomic acids" or a "test genomic sample" refers to genomic nucleic acids comprising sequences whose quantity or degree of representation (e.g., copy number) or sequence identity is being assayed.

As used herein, a "reference nucleic acid sample" or "reference nucleic acids" refers to nucleic acids comprising sequences whose quantity or degree of representation (e.g., copy number) or sequence identity is known. Similarly, "reference genomic acids" or a "reference genomic sample" refers to genomic nucleic acids comprising sequences whose quantity or degree of representation (e.g., copy number) or sequence identity is known. A "reference nucleic acid sample" may be derived independently from a "test nucleic acid sample," i.e., the samples can be obtained from different organisms or different cell populations of the sample organism. However, in certain embodiments, a reference nucleic acid is present in a "test nucleic acid sample" which comprises one or more sequences whose quantity or identity or degree of representation in the sample is unknown while containing one or more sequences (the reference sequences) whose quantity or identity or degree of representation in the sample is known. The reference nucleic acid may be naturally present in a sample (e.g., present in the cell from which the sample was obtained) or may be added to or spiked in the sample.

A "negative control" probe or feature refers to a probe or feature that is designed not to bind with any of the sequences in the sample that is applied to the array on which the negative control probe or feature resides.

A "CGH array" or "aCGH array" refers to an array that can be used to compare DNA samples for relative differences in copy number. In general, an aCGH array can be used in any assay in which it is desirable to scan a genome with a sample of nucleic acids. For example, an aCGH array can be used in location analysis as described in U.S. Pat. No. 6,410,243, the entirety of which is incorporated herein. In certain aspects, a CGH array provides probes for screening or scanning a genome of an organism and comprises probes from a plurality of regions of the genome. In one aspect, the array comprises probe sequences for scanning an entire chromosome arm, wherein probes targets are separated by at least about 500 bp, at least about 1 kb, at least about 5 kb, at least about 10 kb, at least about 25 kb, at least about 50 kb, at least about 100 kb, at least about 250 kb, at least about 500 kb and at least about 1 Mb. In another aspect, the array comprises probes sequences for scanning an entire chromosome, a set of chromosomes, or the complete complement of chromosomes forming the organism's genome. By "resolution" is meant the spacing on the genome between sequences found in the probes on the array. In some embodiments (e.g., using a large number of probes of high complexity) all sequences in the genome can be present in the array. The spacing between different locations of the genome that are represented in the probes may also vary, and may be uniform, such that the spacing is substantially the same between sampled regions, or non-uniform, as desired. An assay performed at low resolution on one array, e.g., comprising probe targets separated by larger distances, may be repeated at higher resolution on another array, e.g., comprising probe targets separated by smaller distances.

In certain aspects, in constructing the arrays, both coding and non-coding genomic regions are included as probes, whereby "coding region" refers to a region comprising one or more exons that is transcribed into an mRNA product and from there translated into a protein product, while by non-coding region is meant any sequences outside of the exon regions, where such regions may include regulatory sequences, e.g., promoters, enhancers, untranslated but transcribed regions, introns, origins of replication, telomeres, etc. In certain embodiments, one can have at least some of the probes directed to non-coding regions and others directed to coding regions. In certain embodiments, one can have all of the probes directed to non-coding sequences. In certain embodiments, one can have all of the probes directed to coding sequences. In certain other aspects, individual probes comprise sequences that do not normally occur together, e.g., to detect gene rearrangements, for example.

In some embodiments, at least 5% of the polynucleotide probes on the solid support hybridize to regulatory regions of a nucleotide sample of interest while other embodiments may have at least 30% of the polynucleotide probes on the solid support hybridize to exonic regions of a nucleotide sample of interest. In yet other embodiments, at least 50% of the polynucleotide probes on the solid support hybridize to intergenic (e.g., non-coding) regions of a nucleotide sample of interest. In certain aspects, probes on the array represent random selection of genomic sequences (e.g., both coding and non-coding). However, in other aspects, particular regions of the genome are selected for representation on the array, e.g., such as CpG islands, genes belonging to particular pathways of interest or whose expression and/or copy number are associated with particular physiological responses of interest (e.g., disease, such a cancer, drug resistance, toxological responses and the like). In certain aspects, where particular genes are identified as being of interest, intergenic regions proximal to those genes are included on the array along with, optionally, all or portions of the coding sequence corresponding to the genes. In one aspect, at least about 100 bp, 500 bp, 1,000 bp, 5,000 bp, 10,000 bp or even 100,000 bp of genomic DNA upstream of a transcriptional start site is represented on the array in discrete or overlapping sequence probes. In certain aspects, at least one probe sequence comprises a motif sequence to which a protein of interest (e.g., such as a transcription factor) is known or suspected to bind.

In certain aspects, repetitive sequences are excluded as probes on the arrays. However, in another aspect, repetitive sequences are included.

The choice of nucleic acids to use as probes may be influenced by prior knowledge of the association of a particular chromosome or chromosomal region with certain disease conditions. International Application WO 93/18186 provides a list of exemplary chromosomal abnormalities and associated diseases, which are described in the scientific literature. Alternatively, whole genome screening to identify new regions subject to frequent changes in copy number can be performed using the methods of the present invention discussed further below.

In some embodiments, previously identified regions from a particular chromosomal region of interest are used as probes. In certain embodiments, the array can include probes which "tile" a particular region (e.g., which have been identified in a previous assay or from a genetic analysis of linkage), by which is meant that the probes correspond to a region of interest as well as genomic sequences found at defined intervals on either side, i.e., 5' and 3' of, the region of interest, where the intervals may or may not be uniform, and may be tailored with respect to the particular region of interest and the assay objective. In other words, the tiling density may be tailored based on the particular region of interest and the assay objective. Such "tiled" arrays and assays employing the same are useful in a number of applications, including applications where one identifies a region of interest at a first resolution, and then uses tiled array tailored to the initially identified region to further assay the region at a higher resolution, e.g., in an iterative protocol.

In certain aspects, the array includes probes to sequences associated with diseases associated with chromosomal imbalances for prenatal testing. For example, in one aspect, the array comprises probes complementary to all or a portion of chromosome 21 (e.g., Down's syndrome), all or a portion of the X chromosome (e.g., to detect an X chromosome deficiency as in Turner's Syndrome) and/or all or a portion of the Y chromosome Klinefelter Syndrome (to detect duplication of an X chromosome and the presence of a Y chromosome), all or a portion of chromosome 7 (e.g., to detect William's Syndrome), all or a portion of chromosome 8 (e.g., to detect Langer-Giedon Syndrome), all or a portion of chromosome 15 (e.g., to detect Prader-Willi or Angelman's Syndrome, all or a portion of chromosome 22 (e.g., to detect Di George's syndrome).

Other "themed" arrays may be fabricated, for example, arrays including whose duplications or deletions are associated with specific types of cancer (e.g., breast cancer, prostate cancer and the like). The selection of such arrays may be based on patient information such as familial inheritance of particular genetic abnormalities. In certain aspects, an array for scanning an entire genome is first contacted with a sample and then a higher-resolution array is selected based on the results of such scanning.

Themed arrays also can be fabricated for use in gene expression assays, for example, to detect expression of genes involved in selected pathways of interest, or genes associated with particular diseases of interest.

In one embodiment, a plurality of probes on the array are selected to have a duplex $T_m$ within a predetermined range. For example, in one aspect, at least about 50% of the probes have a duplex $T_m$ within a temperature range of about 75° C. to about 85° C. In one embodiment, at least 80% of said polynucleotide probes have a duplex $T_m$ within a temperature range of about 75° C. to about 85° C., within a range of about 77° C. to about 83° C., within a range of from about 78° C. to about 82° C. or within a range from about 79° C. to about 82° C. In one aspect, at least about 50% of probes on an array have range of $T_m$'s of less than about 4° C., less then about 3° C., or even less than about 2° C., e.g., less than about 1.5° C., less than about 1.0° C. or about 0.5° C.

The probes on the microarray, in certain embodiments have a nucleotide length in the range of at least 30 nucleotides to 200 nucleotides, or in the range of at least about 30 to about 150 nucleotides. In other embodiments, at least about 50% of the polynucleotide probes on the solid support have the same nucleotide length, and that length may be about 60 nucleotides.

In certain aspects, longer polynucleotides may be used as probes. In addition to the oligonucleotide probes described above, cDNAs, or inserts from phage BACs (bacterial artificial chromosomes) or plasmid clones, can be arrayed. Probes may therefore also range from about 201-5000 bases in length, from about 5001-50,000 bases in length, or from about 50,001-200,000 bases in length, depending on the platform used. If other polynucleotide features are present on a subject array, they may be interspersed with, or in a separately-hybridizable part of the array from the subject oligonucleotides.

In still other aspects, probes on the array comprise at least coding sequences.

In one aspect, probes represent sequences from an organism such as *Drosophila melanogaster, Caenorhabditis elegans*, yeast, zebrafish, a mouse, a rat, a domestic animal, a companion animal, a primate, a human, etc. In certain aspects, probes representing sequences from different organisms are provided on a single substrate, e.g., on a plurality of different arrays.

A "CGH assay" using an aCGH array can be generally performed as follows. In one embodiment, a population of nucleic acids contacted with an aCGH array comprises at least two sets of nucleic acid populations, which can be derived from different sample sources. For example, in one aspect, a target population contacted with the array comprises a set of target molecules from a reference sample and from a test sample. In one aspect, the reference sample is from an organism having a known genotype and/or phenotype, while the test sample has an unknown genotype and/or phenotype or a genotype and/or phenotype that is known and is different from that of the reference sample. For example, in one aspect, the reference sample is from a healthy patient while the test sample is from a patient suspected of having cancer or known to have cancer.

In one embodiment, a target population being contacted to an array in a given assay comprises at least two sets of target populations that are differentially labeled (e.g., by spectrally distinguishable labels). In one aspect, control target molecules in a target population are also provided as two sets, e.g., a first set labeled with a first label and a second set labeled with a second label corresponding to first and second labels being used to label reference and test target molecules, respectively.

In one aspect, the control target molecules in a population are present at a level comparable to a haploid amount of a gene represented in the target population. In another aspect, the control target molecules are present at a level comparable to a diploid amount of a gene. In still another aspect, the control target molecules are present at a level that is different from a haploid or diploid amount of a gene represented in the target population. The relative proportions of complexes formed labeled with the first label vs. the second label can be used to evaluate relative copy numbers of targets found in the two samples.

In certain aspects, test and reference populations of nucleic acids may be applied separately to separate but identical arrays (e.g., having identical probe molecules) and the signals from each array can be compared to determine relative copy numbers of the nucleic acids in the test and reference populations.

Methods to fabricate arrays are described in detail in U.S. Pat. Nos. 6,242,266; 6,232,072; 6,180,351; 6,171,797 and 6,323,043. As already mentioned, these references are incorporated herein by reference. Other drop deposition methods can be used for fabrication, as previously described herein. Also, instead of drop deposition methods, photolithographic array fabrication methods may be used. Interfeature areas need not be present particularly when the arrays are made by photolithographic methods as described in those patents.

Following receipt by a user, an array will typically be exposed to a sample and then read. Reading of an array may be accomplished by illuminating the array and reading the location and intensity of resulting fluorescence at multiple regions on each feature of the array. For example, a scanner may be used for this purpose is the AGILENT MICROARRAY SCANNER manufactured by Agilent Technologies, Palo, Alto, Calif. or other similar scanner. Other suitable apparatus and methods are described in U.S. Pat. Nos. 6,518, 556; 6,486,457; 6,406,849; 6,371,370; 6,355,921; 6,320,196; 6,251,685 and 6,222,664. Scanning typically produces a scanned image of the array which may be directly inputted to a feature extraction system for direct processing and/or saved in a computer storage device for subsequent processing. However, arrays may be read by any other methods or apparatus than the foregoing, other reading methods including other optical techniques or electrical techniques (where each feature is provided with an electrode to detect bonding at that feature in a manner disclosed in U.S. Pat. Nos. 6,251,685, 6,221,583 and elsewhere).

An array is "addressable" when it has multiple regions of different moieties, i.e., features (e.g., each made up of different oligonucleotide sequences or proteins) such that a region (i.e., a "feature" or "spot" of the array) at a particular predetermined location (i.e., an "address") on the array will detect a particular solution phase nucleic acid sequence or protein. Array features are typically, but need not be, separated by intervening spaces.

Figure 3:
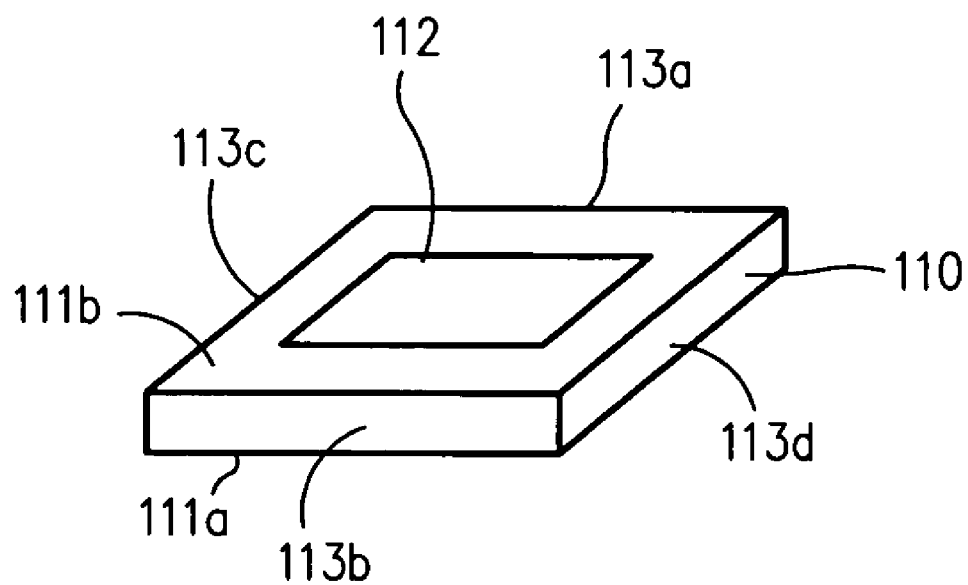
FIG. 3 illustrates an exemplary chemical array.
Figure 4:
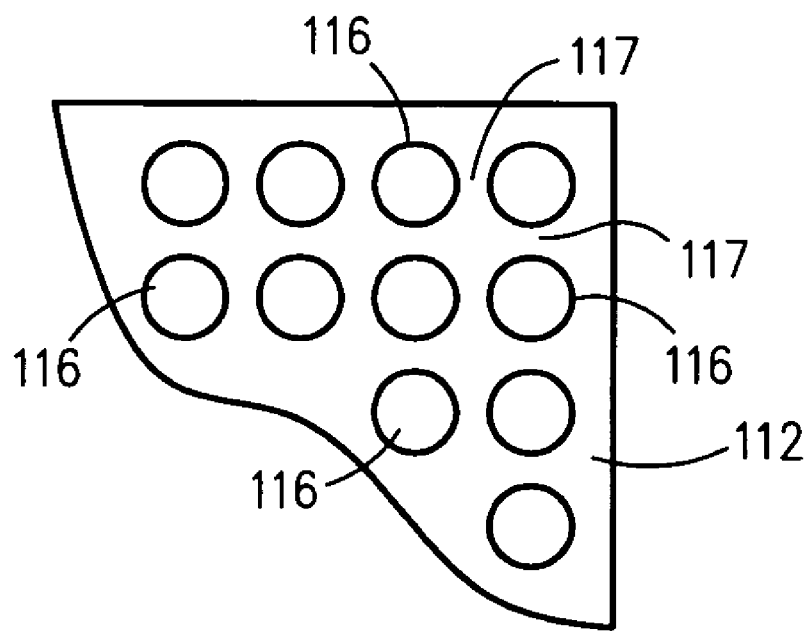
FIG. 4 illustrates an enlarged view of a portion of the array of FIG. 3.

An exemplary array is shown in FIGS. 3-4, where the array shown in this representative embodiment includes a contiguous planar substrate 110 carrying an array 112 disposed on a surface 111b of substrate 110. It will be appreciated though, that more than one array (any of which are the same or different) may be present on surface 111b, with or without spacing between such arrays. That is, any given substrate may carry one, two, four or more arrays disposed on a surface of the substrate and depending on the use of the array, any or all of the arrays may be the same or different from one another and each may contain multiple spots or features. The one or more arrays 112 usually cover only a portion of the surface 111b, with regions of the surface 111b adjacent the opposed sides 113c, 113d and leading end 113a and trailing end 113b of slide 110, not being covered by any array 112. An opposite surface 111a of the slide 110 typically does not carry any arrays 112. Each array 112 can be designed for testing against any type of sample, whether a trial sample, reference sample, a combination of them, or a known mixture of biopolymers such as polynucleotides. Substrate 110 may be of any shape, as mentioned above.

As mentioned above, array 112 contains multiple spots or features 116 of oligomers, e.g., in the form of polynucleotides, and specifically oligonucleotides. As mentioned above, all of the features 116 may be different, or some or all could be the same. The interfeature areas 117 could be of various sizes and configurations. Each feature carries a predetermined oligomer such as a predetermined polynucleotide (which includes the possibility of mixtures of polynucleotides). It will be understood that there may be a linker molecule (not shown) of any known types between the surface 111b and the first nucleotide.

Substrate 110 may carry on surface 111a, an identification code, e.g., in the form of bar code (not shown) or the like printed on a substrate in the form of a paper label attached by adhesive or any convenient means. The identification code may contain information relating to array 112, where such information may include, but is not limited to, an identification of array 112, i.e., layout information relating to the array (s), etc.

In the case of an array in the context of the present application, the "target" may be referenced as a moiety in a mobile phase (typically fluid), to be detected by "probes" which are bound to the substrate at the various regions.

A "scan region" refers to a contiguous (preferably, rectangular) area in which the array spots or features of interest, as defined above, are found or detected. Where fluorescent labels are employed, the scan region is that portion of the total area illuminated from which the resulting fluorescence is detected and recorded. Where other detection protocols are employed, the scan region is that portion of the total area queried from which resulting signal is detected and recorded. For the purposes of this invention and with respect to fluorescent detection embodiments, the scan region includes the entire area of the slide scanned in each pass of the lens, between the first feature of interest, and the last feature of interest, even if there exist intervening areas that lack features of interest.

An "array layout" refers to one or more characteristics of the features, such as feature positioning on the substrate, one or more feature dimensions, and an indication of a moiety at a given location. "Hybridizing" and "binding", with respect to nucleic acids and/or proteins, are used interchangeably.

A "design file" is typically provided by an array manufacturer and is a file that embodies all the information that the array designer from the array manufacturer considered to be pertinent to array interpretation. For example, Agilent Technologies supplies its array users with a design file written in the XML language that describes the geometry as well as the biological content of a particular array.

A "design pattern" is a description of relative placement of features, with annotation. A grid template or design pattern can be generated from parsing a design file and can be saved/stored on a computer storage device. A grid template has basic grid information from the design file that it was generated from, which information may include, for example, the number of rows in the array from which the grid template was generated, the number of columns in the array from which the grid template was generated, column spacings, subgrid row and column numbers, if applicable, spacings between subgrids, number of arrays/hybridizations on a slide, etc. An alternative way of creating a grid template is by using an interactive grid mode provided by the system, which also provides the ability to add further information, for example, such as subgrid relative spacings, rotation and skew information, etc.

A "property" of an array, as used herein refers to a characteristic of an array that may be measured through analysis and calculation based on signals received during reading (e.g., scanning or other method of obtaining signals from) the array, and which may be used as a measure of quality of the array.

Properties include, but are not limited to, noise, signal-to noise, background signal, signal intensity, uniformity/non-uniformity, etc.

A "probe signal", "probe value" or "probe signal value" refers to the observed signal obtained from the probe, i.e., the signal from a probe bound to a target, including "true" signal (i.e., the target that the probe was designed to bind with) and offset, such as from cross-hybridization and other noise factors, including background).

When one item is indicated as being "remote" from another, this is referenced that the two items are not at the same physical location, e.g., the items are at least in different buildings, and may be at least one mile, ten miles, or at least one hundred miles apart.

"Communicating" information references transmitting the data representing that information as electrical signals over a suitable communication channel (for example, a private or public network).

"Forwarding" an item refers to any means of getting that item from one location to the next, whether by physically transporting that item or otherwise (where that is possible) and includes, at least in the case of data, physically transporting a medium carrying the data or communicating the data.

A "processor" references any hardware and/or software combination which will perform the functions required of it. For example, any processor herein may be a programmable digital microprocessor such as available in the form of a mainframe, server, or personal computer. Where the processor is programmable, suitable programming can be communicated from a remote location to the processor, or previously saved in a computer program product. For example, a magnetic or optical disk may carry the programming, and can be read by a suitable disk reader communicating with each processor at its corresponding station.

Reference to a singular item, includes the possibility that there are plural of the same items present.

"May" means optionally.

Methods recited herein may be carried out in any order of the recited events which is logically possible, as well as the recited order of events.

All patents and other references cited in this application, are incorporated into this application by reference except insofar as they may conflict with those of the present application (in which case the present application prevails).

Methods, Systems and Computer Readable Media

In general, the intensity associated with a feature of a chemical array may be expressed as the sum of: (1) a first signal-intensity component produced by bound target molecule labels; and (2) a second signal-intensity component, referred to as the "background," which may be the product of a wide variety of background-intensity-producing sources, including noise produced by electronic and optical components of a microarray scanner, general non-specific reflection of light from the surface of the microarray during scanning, or, in the case of radio-labeled target molecules, natural sources of background radiation, and various defects and contaminants on, and damage associated with, the surface of the microarray. Background may also be the result of a contaminant bound to the probes, or to an underlying silane layer, or impurities in glass underlying the silane layer. Background signal may also be due to varying amounts of non-specific binding of labeled target.

Alternatively, the "background" referred to above is sometimes broken down into separate groups of sources referred to as background and foreground. Under this classification, the background refers to signal-intensity components that are present on the interfeature surfaces of the array, such as those that may be caused by the glass or other substrate of the array itself, hybridization artifacts, etc., and foreground refers to the additional signal-intensity components on the features that are not attributable to the target bound thereto, but may be caused by non-specific binding of labeled target, contamination bound to the probes, etc.

The background may also contain signal intensities resulting from signals emitted by probes bound to a feature, which in turn, may be the result of weak intrinsic fluorescent properties of probe molecules and a stronger contribution induced by radiation used to stimulate emission from hybridized target molecule labels. The signals emitted by bound probe nucleotides may be sequence dependent. For example, in the case of the signal strengths produced by the four DNA nucleotide bases background signal emitted by individual nucleotides vary from a relatively weak signal produced by deoxy-adenosine, to intermediate signal strengths produced by deoxy-thymidine and deoxy-guanosine, in that order of respective strengths, to a relatively strongest signal-intensity produced by deoxy-cytosine. Therefore, oligonucleotide probes with a high proportion of A's produce smaller second signal intensity components, while oligonucleotide probes with a high proportion of C's produce larger second signal intensity component. The strength of the induced signal emitted by probes may also be proportional to the nucleotide sequence mass.

Ideally, randomly distributed array features having bound probes with identical nucleotide sequences should emit substantially identical signal intensity when measured by an array reader. A variation in signal or background intensities across an array surface is referred to as a "spatial-intensity trend." or "gradient", as noted above. A scanning of a chemical array that uses fluorescently marked probes stores a collection of light intensity values of the pixels in the image of the chemical array having been scanned. The intensity values stored are all positive numbers offset from zero by a small amount, typically a few tens of counts of intensity. Further, there typically exists some residual fluorescence all over the array, as well as more specifically on each feature, which leads to another added offset to the data, described as the foreground above. Because these various offsets in the data are not easily known, this also makes it difficult to determine the baseline or "zero: intensity level against which to measure the intensities of the signal measurements of the feature that are attributable to the targets bound thereto, i.e., it is difficult to determine the physical signal measurement of a feature with zero biological specific binding, and this is left as a post-processing task on the scanned image of the array.

In order to carry out such post-processing according, the present invention takes advantage of the fact that most array designs reserve a certain number of the features on the array for sequences that are designed not to bind with any of the sequences in the target sample that is applied to the array. These features are typically called negative controls. Thus, the measurement of the negative control features should be a good estimate of the signal of a feature with zero target bindings. In practice, however, the negative control probes may be too different from the remainder of the probes on the array to be completely representative of those remaining features with regard to possible offsets, typically foreground, such as random bindings, sequence-dependent contamination, or other sources of offset. Additionally or alternatively, there may be too few negative control features to provide a precise reference over all of the surface of the array, and this can be problematic when gradients exist, for example.

Thus, a secondary approach taken herein addresses the issue that, statistically, a significant number of probes on an array will represent information (genetic information, or other extraneous chemical or biological information) that is not present in the sample (target) that is intended to be measured. Therefore, the population of the lowest intensity signals is expected to be a measure of probes with very little or no bonding. However, it is typically difficult to identify a spread or distribution of these low intensity signals from a histogram of the intensity signals read from an array, because the intensity values from the overall array typically represent a continuum of values from zero to very large values, and because the intensity values are further spread out due to the offset signals described above, and these offset signals may vary in different areas of the array (e.g., as in the case where a gradient is present).

Finding the intensity values of the features considered to represent zero intensity (no target binding) and the spread of such values is important for at least two reasons. The offset as defined by the intensity value of what is considered to be "zero" (i.e., no target binding, such that the intensity of such a feature represents only intensity from offset) needs to be subtracted from each measured intensity value per feature read from the array to provide accurate measurements of the sample being assayed by the array. Note that such post-processing may be performed for more than one channel of signal intensity readings, such as, for example, arrays from which two channels of information are read (e.g., "red" and "green" channels). The post-processing described is carried out individually with regard to each channel, as offsets may vary from channel to channel. The post-processing is not limited to single channel arrays or two-channel arrays, as the same processing may be carried out for arrays in which more than two channels of information are read and processed. The spread of values around "zero" is an important parameter for evaluating the precision of the measurements of all signals across the array. To calculate spread, a standard deviation or inter-quartile range of signals is considered (optionally excluding outliers or features otherwise flagged, such as for saturation, non-uniformity, etc.). Feature signals that are five times the normalized inter-quartile range (where inter-quartile range is a robust way of calculating standard deviation) or standard deviation away from the $25^{th}$ or $75^{th}$ percentile, for the lower and upper range, respectively, of the signal population are excluded from the computation of the spread. It should be noted that this is just one example of setting upper and lower limits, as the multiplier for the interquartile ranges does not have to be five, but can be adjusted. For example, the multiplier may take on any value between about one and about 10. The spread is calculated as the square root of the sum of the squares of the deviation from the fitted value for each negative control signal.

Figure 5:
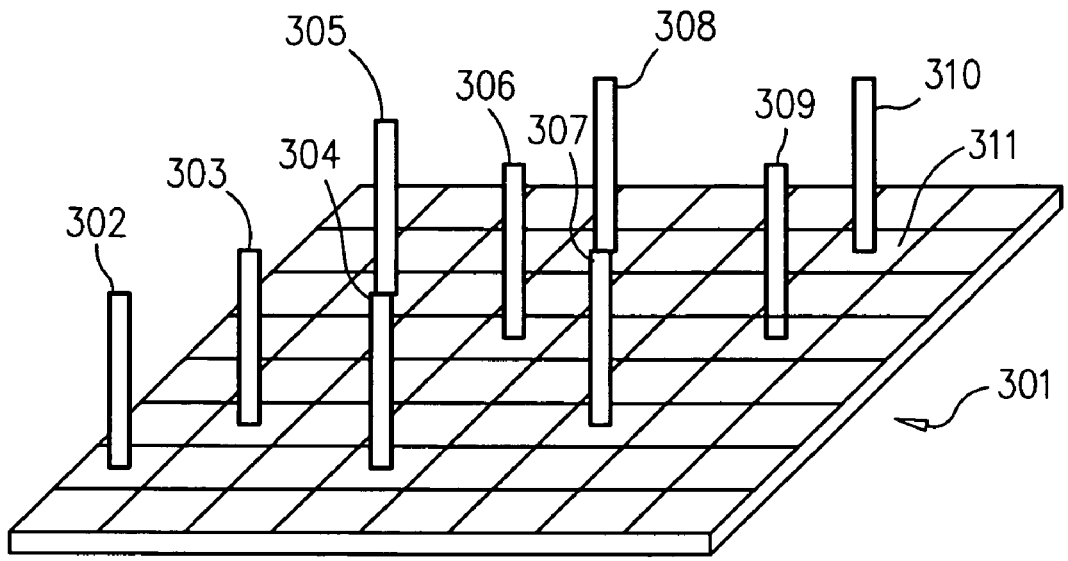
FIG. 5 illustrates an ideal, hypothetical chemical array having no spatial-intensity trend.
Figure 6:
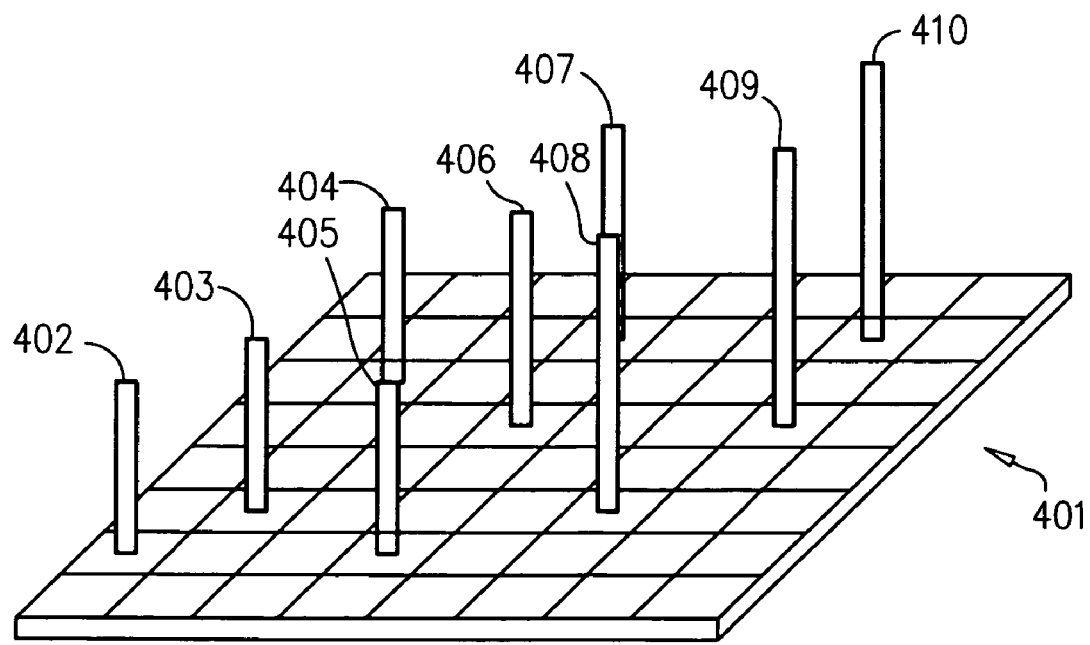
FIG. 6 illustrates a hypothetical chemical array having a spatial-intensity trend.

FIG. 5 schematically illustrates an ideal, hypothetical chemical array having no apparent spatial-intensity trend. In FIG. 5, the red-channel, lowest-signal-intensity features of the array 301 are identified by bars 302-310 extending above the array surface. The height of each bar represents the signal-intensity strength emitted by the corresponding feature below. For example, the height of bar 310 above feature 311 represents the red-signal-intensity strength emitted by feature 311. Because the bars 302-311 are all approximately the same height, there appears to be no spatial-intensity trend present for the red channel of the array 301. In contrast, FIG. 6 illustrates a hypothetical chemical array having an apparent spatial-intensity trend. In FIG. 6, the red-channel, lowest-signal-intensity features of array 401 are identified by bars 402-410. The spatial-intensity trend is observed by the increase in the height of bars from left to right. For example, bars 402-404 are shorter than the bars 405-407, which, in turn, are shorter than bars 408-410.

Figure 7A:
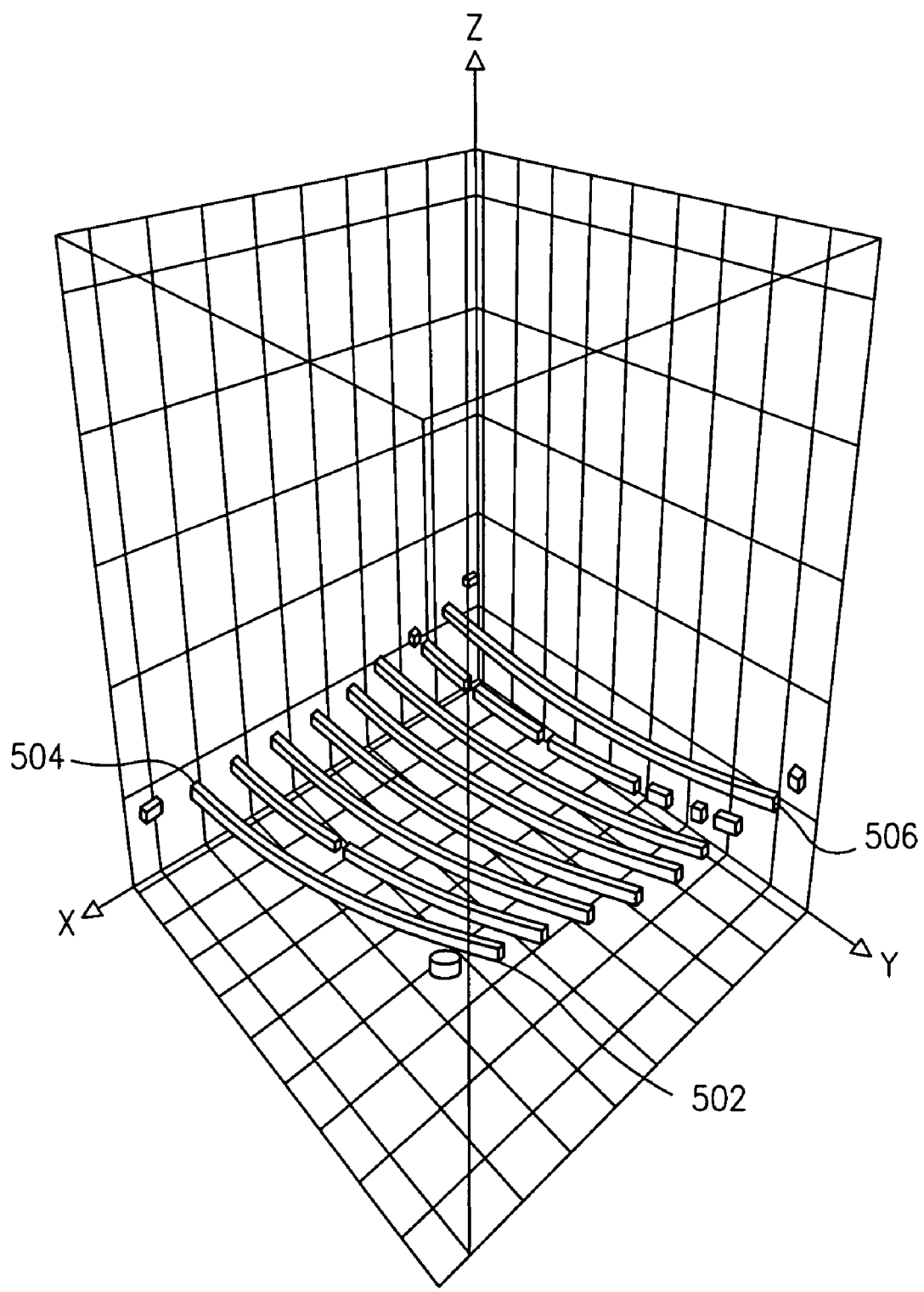
FIG. 7A shows surface intensity values calculated for negative control features selected from a chemical array.
Figure 7B:
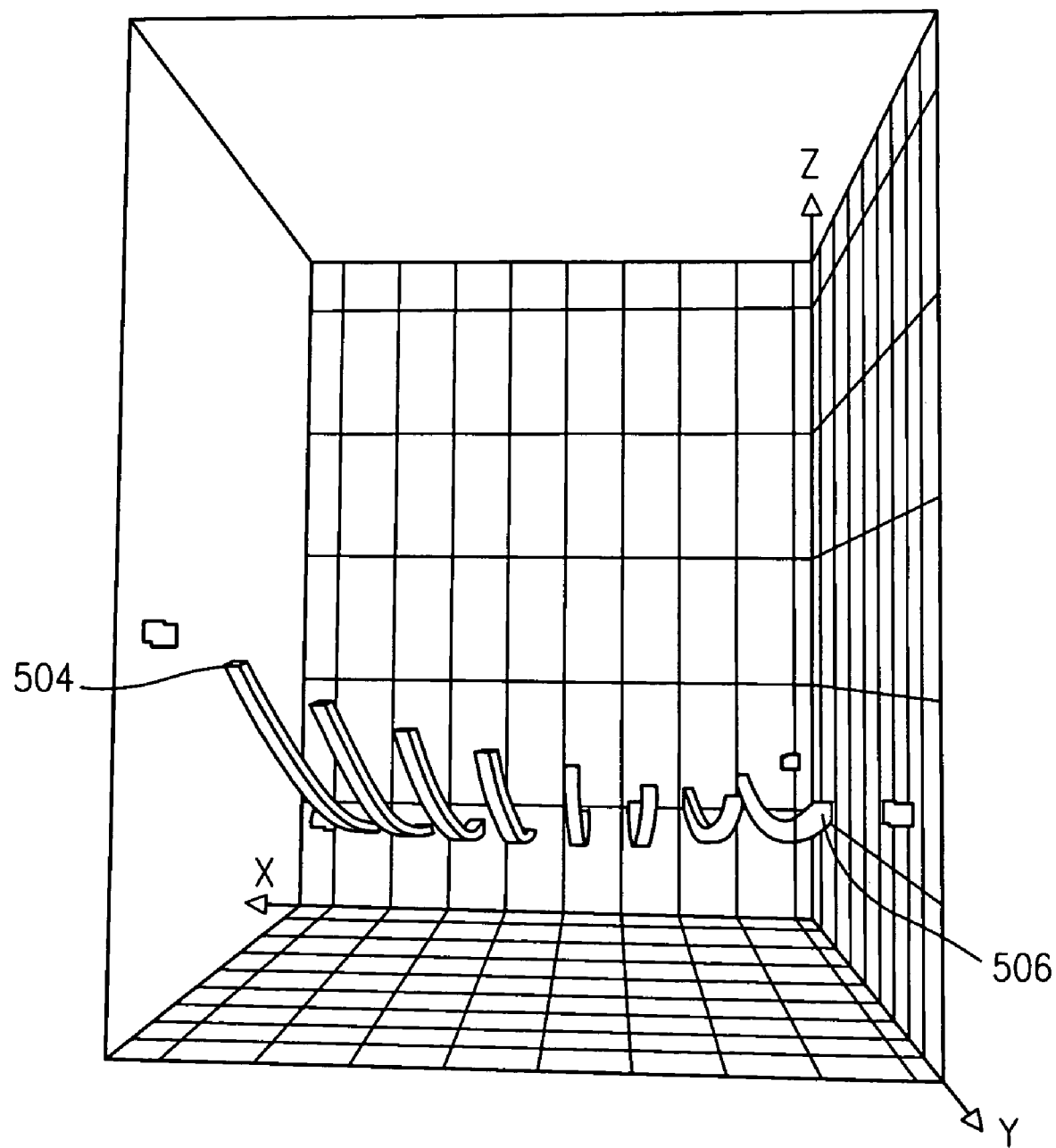
FIG. 7B show a rotated view of FIG. 7A in which the view of FIG. 7A has been rotated by 45 degrees about the Z-axis.

FIGS. 7A-7B show plots of the intensity values read from negative control probes, wherein the X-axis plots row values of the array on which the features are located, the Y-axis plots the column values of the features on the array, and the Z axis plots the intensity values read. As can be seen in FIG. 7A, the intensity value of feature 502 (i.e., value along the Z-axis) is greater than that for feature 504, and is also greater than that for feature 506. Thus, there is a gradient in the intensity readings of the negative control features in both the X and Y directions. FIG. 7B is a rotated view of FIG. 7A that more clearly shows the gradient in the X direction. The plots in FIGS. 7A and 7B are the result of a preliminary fit in the post-processing that fits the negative control feature intensity signals to a spatial surface to give a preliminary estimate of the spatial bias of all signal data from the array.

Although FIGS. 7A-7B relate to spatial intensity trends or gradients observed in the intensities from negative control features, which tend to be features with no specifically bound target molecule labels, such gradients may also be observed in the other features on the array, including the highest signal intensity features. For example, spatial-intensity trends due to artifacts of hybridization or wash tend to show up in the highest-signal intensity features. A spatial-intensity trend in the brighter features is often proportional to the intensity of the signal. In other words, the spatial-intensity trend is a multiplier to the signal intensity. For example, a feature having a signal intensity of 1000 may be increased to 1100, while a feature having a signal intensity of 10,000 may be increased to 11,000. For example, synthesis and hybridization/wash steps are all directional step with regard to the array and typically proceed from one end of the array to the other (e.g., left to right or vice versa). Thus, is there is a problem with one of these processes, the error induced by the problem (resulting in offset signal) often increases in the direction that the process was applied.

Figure 8:
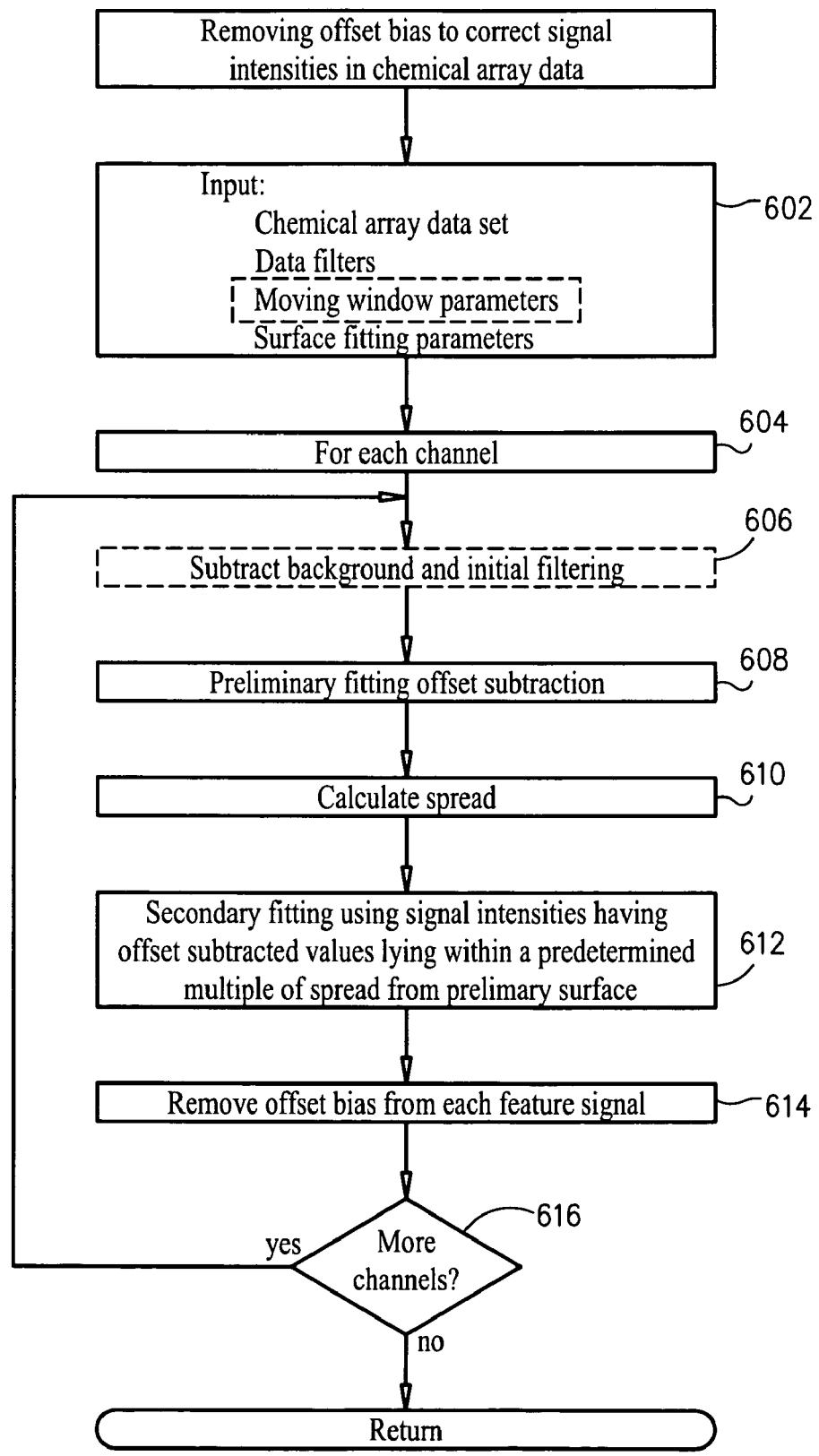
FIG. 8 is a control-flow diagram that describes one of many possible embodiments of the present invention.

One of many possible embodiments of the present invention is directed to a method for detecting, quantifying, and correcting offset signals causing spatial-intensity trends in chemical array data. FIG. 8 is a control-flow diagram that describes one of many possible embodiments of the present invention. The method diagrammed in FIG. 8 is discussed below with reference to FIG. 8, FIGS. 7A-7B and to subsequent figures that provide greater detail for many of the events shown in FIG. 8.

At event 602, a user interface may be employed to receive a chemical array data set, which may be a single channel or multi-channel chemical array data set. Data filters may be inputted for initially filtering the data, and optionally, moving window parameters and or sampling parameters may be inputted, such as size, increment, and fraction of features selected. Best-fit surface parameters may also be inputted. The data set may comprise two data subsets corresponding to two different channels of one chemical array, or may comprise one data subset corresponding to signals obtained from one channel of a chemical array, or may comprise more than two data subsets when more than two channels of an array are present. The feature intensities of the data set can be provided in many forms, including raw intensities, background-subtracted intensities, and signal-intensity ratios for features generated form signals obtained from two different channels.

Figure 9:
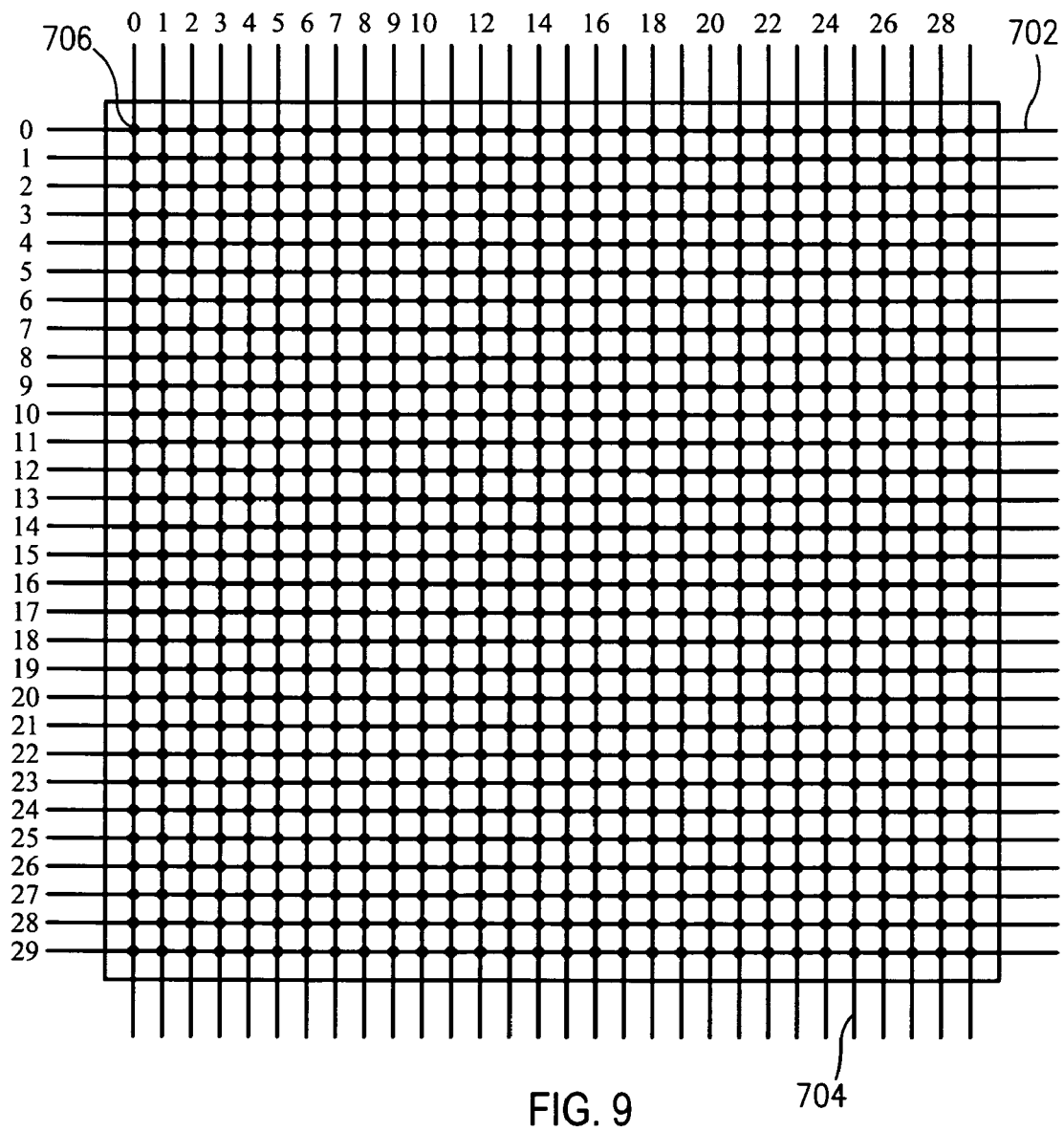
FIG. 9 illustrates indexing features of a chemical array.

Each subset of data is indexed to provide location coordinates for each feature. FIG. 9 illustrates indexing of features of a chemical array. A set of horizontal and vertical grid lines, such as horizontal line 702 and vertical line 704, are arranged so that the intersections of horizontal and vertical grid lines correspond to centers of features. The imaginary grid lines establish a two-dimensional index grid for indexing the array features. The entire set of array features may thus be denoted by $\{(x, y), I, c\}$, where $(x, y)$ corresponds to the feature coordinates of a feature having signal intensity I, and a channel index c. The total number of microarray features is denoted by L. For example, the coordinates for feature 706 are $(0, 0)$. For alternative arrangements of features, such as offsetting alternating columns of features, a different indexing system may be used. For example, feature location in odd-indexed rows having a particular column index may be understood to be physically offset horizontally from feature locations having the same column index in even-indexed rows. Such horizontal offsets occur, for example, in hexagonal, closest-packed microarrays of features.

At event 604, the for-loop executes steps 606-616 separately for each channel provided in the chemical array data set. At event 606, the background of the array features may be subtracted and initial filtering may be performed. This initial background subtraction is optional and does not greatly affect the results, since the foreground also includes the intensity components present in the background. Thus, if the foreground is subtracted without having first subtracted the background, then the foreground that is subtracted in this case is a combination of foreground and background. Therefore, background can be initially subtracted first, or not, since the background will then be subtracted along with the foreground if it was not initially subtracted. If the initial background subtraction is the type that subtracts local background, that is, the surfaces around and between each feature, then that type of background subtraction removes the signal-intensity components that are present on the interfeature surfaces of the array, such as those that may be caused by the glass or other substrate of the array itself, hybridization artifacts, etc., but not the foreground referred to above. The foreground may contain spatial dependence not seen in the background. Sometime the "shape" of this dependence across an array may be the same, but of different magnitude. For example, the left edge of an array may have brighter background and foreground than the right edge, wherein the foreground is more intense by twenty counts at the left edge versus the right edge and the background is more intense by three counts at the left edge versus the right edge. This background subtraction may be carried out according to a number of different currently existing algorithms. As an example, this background subtraction may be performed according to a method described in co-pending, commonly owned U.S. patent application Ser. No. 10/153,345, filed May 21, 2002 and titled "Method and System for Computing and applying a Global, Multi-Channel Background Correction to Feature-Based Data Set Obtained from Scanning a Molecular Array"; co-pending, commonly owned U.S. patent application Ser. No. 10/859,801, filed Jun. 2, 2004 and titled "Method and System for Computing and Applying a User-Defined, Global, Multi-Channel Background Correction to a Feature-Based Data Set Obtained from Reading a Molecular Array," or U.S. patent application Ser. No. 10/859,868, filed Jun. 2, 2004 and titled "Method and System for Quantifying and Removing Spatial-Intensity Trends in Microarray Data", each of which is incorporated herein, in its entirety, by reference thereto. In addition, the features may be filtered by removing features having signal intensities above a threshold value and irregularly shaped features. For initial filtering, only negative control features are considered and those negative control features determined to be non-uniformity outliers are filtered out. Note that the term "filtered" does not actually mean feature data is removed from the microarray data set. Instead, filtering involves identifying those features that are considered to be outliers and that therefore are not used in surface fitting the data.

Filtering employed at event 606 includes initially filtering all features except negative-control features. Further filters at event 606 may include, but are not limited to: a filter that removes negative control features having a non-uniform intensity distribution, and filtering features that are negative controls but are beyond a predetermined threshold value from the middle of the negative control signal range (e.g., where a low bound filter filters out signals less than the $25^{th}$ percentile$-5*$IQR (inter-quartile range), and a high bound filter filters out signals greater than the $75^{th}$ percentile$+5*$IQR). Note that the multiplier for IQR need not be five but can be varied, e.g. a value from about one to about 10 could be substituted. One way of filtering to remove all features except negative control features employs the design file of the array being analyzed, wherein the design file differentiates negative control features from all other features by coding. Additionally, the design file maps these encoded negative control features to their locations on the array as identified by the array layout. Accordingly, for purposes of the preliminary fit, filtering can then simply ignore those features, for whose locations on the array do not match the information for the negative control features provided by the design file and array layout.

Figure 10A:
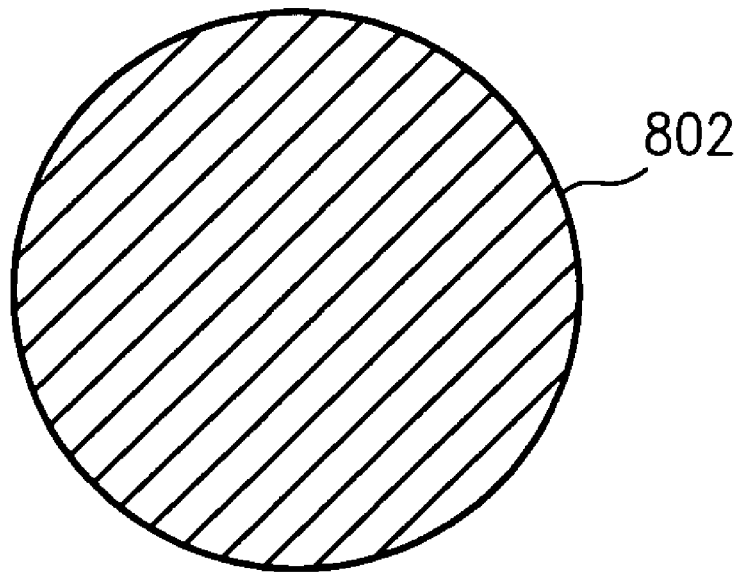
FIG. 10A illustrates a feature having a uniform intensity distribution.
Figure 10B:
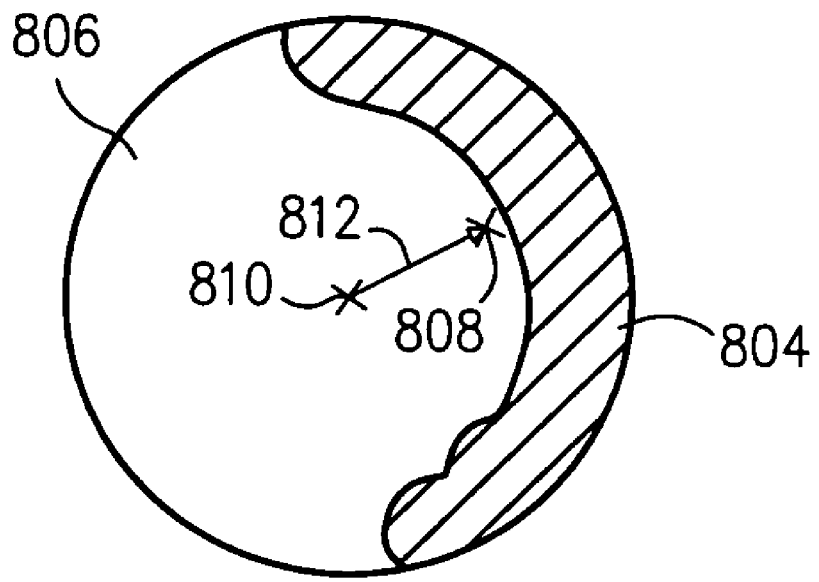
FIG. 10B illustrates a feature having a non-uniform intensity distribution.

A filter designed to remove from consideration features having non-uniform intensity distributions over the area of the features is described with regard to FIGS. 10A-10B. FIG. 10A shows a feature having a uniform intensity distribution and FIG. 10B shows a feature having a non-uniform intensity distribution. In FIG. 10A, the disc-shaped area of the image of a feature 802 is shown with cross-hatching indicating a uniform distribution of moderate intensity values over the entire area of the image of the feature. In contrast, FIG. 10B shows a crescent-shaped portion 804 of the area of a feature 806 having medium intensity values, while the remaining portion of feature, 806 has low intensity values. The signal intensities within the feature shown in FIG. 10B are non-uniformly distributed. Non-uniform distribution of intensities can be detected in a number of different of ways. A statistical variance of pixel intensities within the area of the image of a feature can be computed, and features with pixel-intensity variances greater than a threshold variance can be considered to have non-uniform pixel-intensity distributions. For example, the threshold may be a function of biological or electronic noise, or noise on the microarray due to chemical or hybridization processes. Alternatively, as shown in FIG. 10B, a centroid for the pixel intensity distribution 808 can be computed, and the location of the centroid compared to the location of the geometric center 810 of the image of the feature. When the distance 812 between the centroid of pixel-intensity and the geometric center is greater than a threshold distance value, the feature can be considered to have a non-uniform pixel-intensity distribution. Alternatively, both the mean and the median signal statistics can be computed and a feature can be considered to have a non-uniform pixel-intensity distribution if the difference between the mean signal and the median signal exceeds a threshold or if the difference divided by either the mean or the median signal exceeds a threshold. Many other alternative techniques can be employed in order to classify features having uniform and non-uniform pixel-intensity distributions. At event 606, those negative control features having non-uniform pixel distributions are removed from consideration. As noted above, features in certain types of chemical arrays may not be disc-shaped, and techniques used to compute a metric of uniformity may need to be tailored specifically to the particular feature shapes present in the arrays.

At event 608, the signals from the negative control features that passed any filters applied are used to generate a preliminary surface fit (preliminary fit) in the post-processing that fits these negative control feature intensity signals to a spatial surface to give a preliminary estimate of the spatial bias of all signal data from the array. Examples of negative control features that are used to determine this fit are illustrated in FIGS. 7A and 7B. The entire set of N filtered negative control features selected in event 606 may be denoted by $\{(x_i,y_i),I_i,C\}_{i=1}^{N}$, where $(x_i, y_i)$ specifies the feature coordinates of filtered feature i, $I_i$ represents the corresponding intensity of filtered negative control feature i, and C is the channel index. A set of filtered features $\{(x_i,y_i), I_i,C\}_{i=1}^{N}$ can be used to determine a set of data points, referred to as the "best-fit surface" and denoted by S, that characterizes the spatial-intensity trends for the all of the features in the channel C of the chemical array data and that are surface intensity values on a surface that can be calculated therefrom to describe the spatial intensity trends, since the negative controls are typically randomly distributed over the spatial surface of the array. The set of data points S is constructed by first fitting a best-fit surface to the set of N filtered negative control feature intensity values. This best-fit surface may be determined using any of a number of surface fitting algorithms currently available. Typically, this preliminary surface fit is performed using a second-order polynomial approximation of the surface according to techniques known in the art.

This preliminary fit is typically performed using a second-order polynomial as described because it is fast to compute and has been found to give satisfactory results. However, as noted, other algorithms may be used to calculate the preliminary surface fit. For example, a higher order polynomial may be used, but this entails more computation time and also, the second order polynomial tends to provide a more smooth or rounded result, whereas a fit with a higher order polynomial will fit more data points and therefore tends to capture more data points that, although not filtered out as outliers in event 606, may be near a threshold where they would be considered outliers. The use of the second order polynomial approximation naturally filters out such small perturbations. This provides a robust fit that tends to exclude outliers in calculating the surface fit.

Another algorithm that may be used for approximating the surface for the preliminary fit is a locally-weighted, least-squares method, referred to as "Loess". This algorithm is also more computationally intensive than the use of the second-order polynomial, and so is typically not used for the preliminary fit, although it may be. The Loess method code implemented in the present invention can be obtained from the website http://www.netlib.org/a/dLoess. A written description of the Loess method can be obtained from the website http://www.itl.nist.gov/div898/handbook/pmd/section1/pmd144.htm, (Cleveland, W. S. (1979) "Robust Locally Weighted Regression and Smoothing Scatterplots," *Journal of the American Statistical Association*, Vol. 74, pp. 829-836, and Cleveland, W. S., and Devlin, S. J. (1988) "Locally Weighted Regression: An Approach to Regression Analysis by Local Fitting," *Journal of the American Statistical Association*, Vol. 83, pp. 596-610.)

Figure 11:
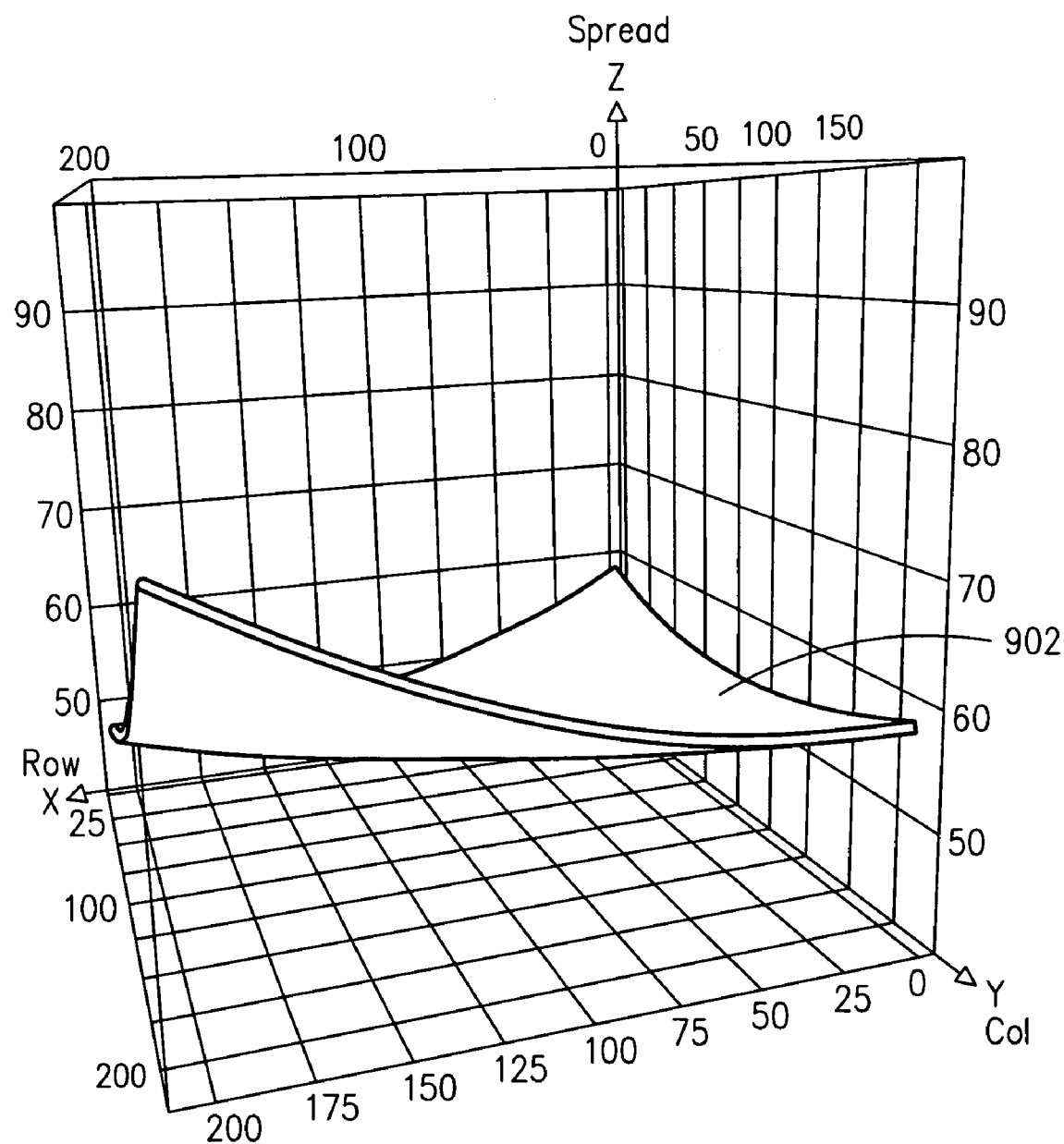
FIG. 11 shows a surface derived from a second order polynomial fit of filtered negative control intensity values from negative control features on a chemical array.

Once the surface approximation has been determined, values for all features (locations) of the array can be calculated using the calculated values for the filtered negative control signals as fit to the surface approximation, because the polynomial fit gives a closed form equation that describes the surface. FIG. 11 shows a surface 902 derived from a second order polynomial fit of filtered negative control intensity values in a manner as described above, and which corresponds to the fitted values for the negative control intensity values shown in FIGS. 7A-7B.

In addition to the consideration that is given to spatial variations in signal intensity due to systematic errors and noise that result in spatial gradients (such as hybridization and wash conditions, synthesis, scanner errors, etc, as discussed above), consideration also needs to be given to potential sequence dependent offset biases. As noted above, different sequences may have different signal sensitivity factors, which may also cause offset biases. Therefore a "zero" value determined by removing offset signal as identified using the negative controls as described may be slightly off for some feature/probes that contain sequences that may be more or less effected that the negative control sequences due to the differences in those sequences. Therefore, further post-processing is conducted to take into account signals from additional low signal features on the array to consider additional sequences of which vary from the negative control feature sequences.

At event 610, the residual from the calculation of the surface 902 is used to calculate the spread of the negative control signal intensities. The spread is determined by computing the differences between the intensity values of the negative control signals and the corresponding values on the surface 902 (in the corresponding locations of the negative control features, respectively), and then calculating the square root of the average of the squares of these terms as follows:

$$\text{Spread} = \sqrt{\frac{\sum_{i=1}^{N} (I_i - S_i)^2}{N}} \qquad (2)$$

where

N=the total number of negative control intensity values used in calculating the surface approximation, I=intensity value of a negative control signal, and S=intensity value of the surface location corresponding to the location of the negative control probe from which I was obtained.

As noted above, filtering may be performed prior to the calculation of the spread to remove from consideration those signals from negative control features that are well out on the distribution of negative control signals (e.g., more than a predetermined number of standard deviations from the center of the negative control feature signal intensity distribution. Also, a robust inter-quartile range can be used for calculation of spread, rather than use of the standard deviation, which was also mentioned previously.

Figure 12:
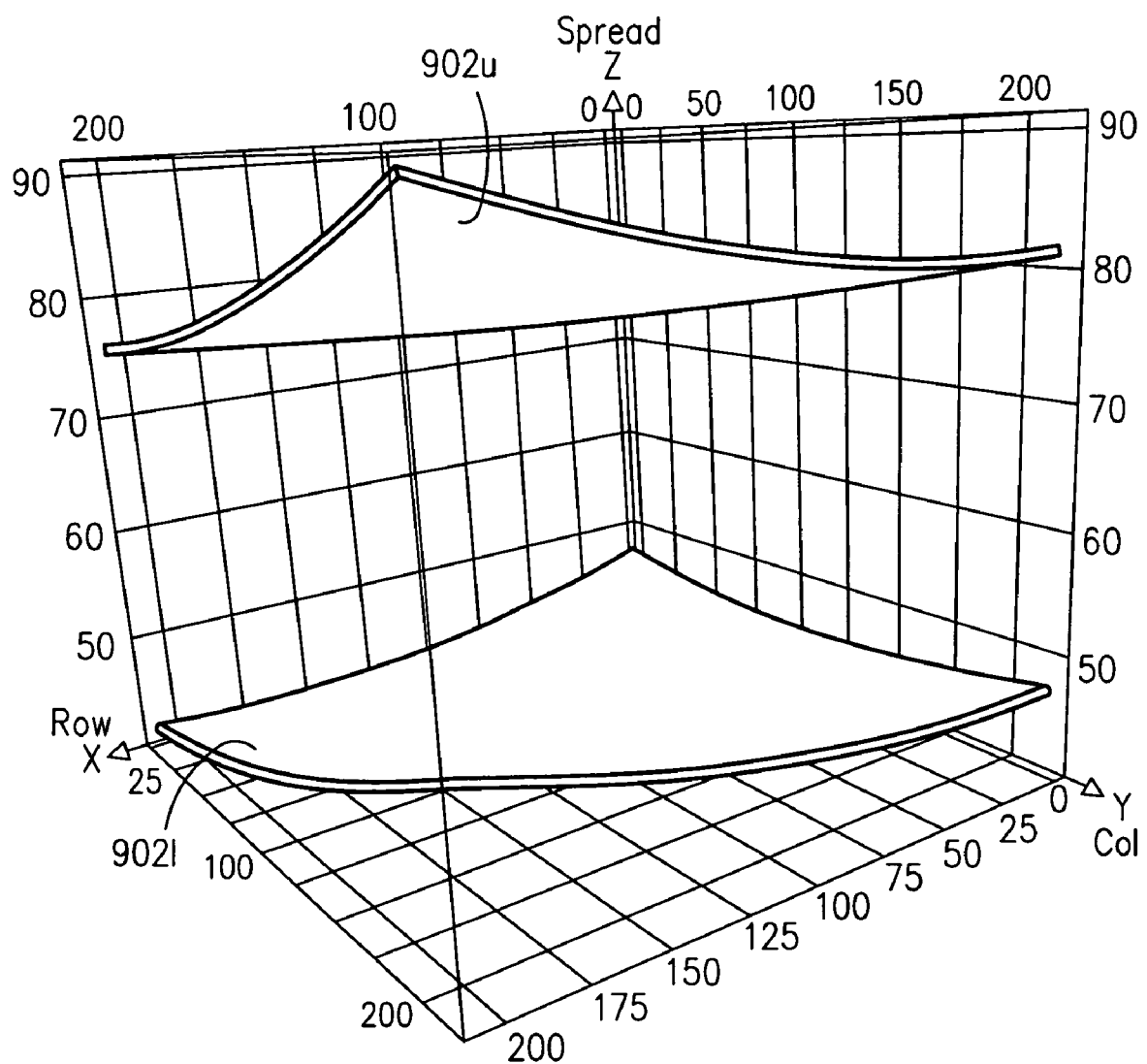
FIG. 12 shows upper and lower threshold surfaces calculated as a function of the surface shown in FIG. 11 and the spread of the negative control intensity values relative to the surface of FIG. 11.

Upon obtaining the spread, this value is then used to move the calculated surface 902 in both negative and positive directions along the intensity axis to be used as an upper limit threshold and a lower limit threshold for filtering signals for the secondary fit described below. FIG. 12 shows the upper and lower threshold surfaces 902u and 902l, respectively, having been established from the surface 902 shown in FIG. 11 after moving each surface 902u and 902l by a multiple of the calculated spread in opposite directions along the intensity (Z or spread) axis. The multiple of the calculated spread may be varied, and may be user selectable, such as through the user interface. In the example shown in FIG. 12, the surfaces 902u and 902l have been moved a distance of three times the calculated spread and thus the predetermined multiple was 3. However, any multiple that makes sense in the user's context may be set. Thus a multiplier of 2, 2.5, 4, 6, or any other multiplier could be substituted, although generally, 3 has been found to generally function well.

Figure 13:
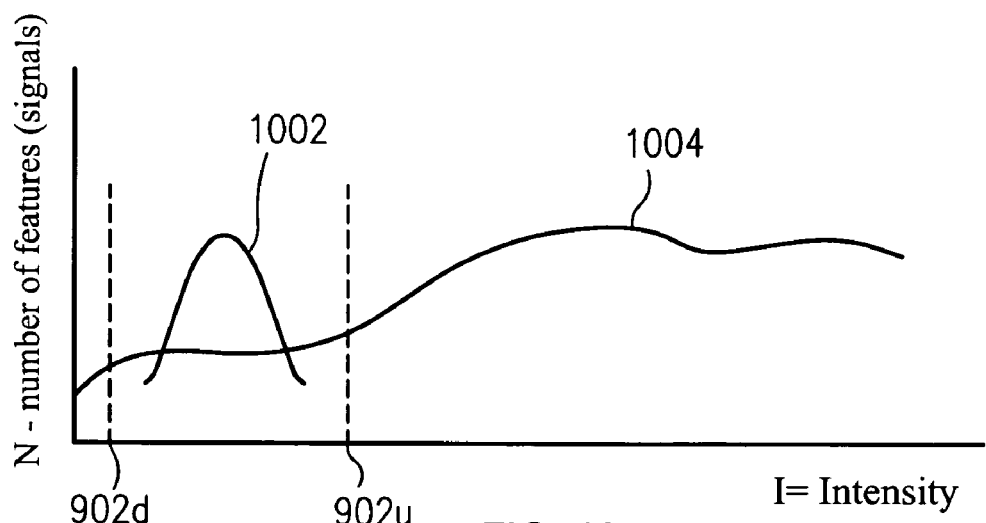
FIG. 13 illustrates a histogram of the intensities and corresponding numbers of negative control feature signals and a histogram of the intensities and corresponding numbers of all other feature signals from a hypothetical chemical array.

FIG. 13 illustrates a histogram 1002 of the intensities and corresponding numbers of negative control feature signals and a histogram 1004 of the intensities and corresponding numbers of all other feature signals from a chemical array. As noted, the preliminary fit can be used to determine a "zero" signal level by removing the spatial offsets identified by characterizing the surface fit of the selected filtered negative control signals. However, this zero level may not be accurate for all feature signals due to sequence dependent offset bias. Thus, after performing the preliminary fit and calculating the spread as indicated, the thresholds 902$u$ and 902$l$ are established and all signal intensity values lying between these thresholds may be used to perform a secondary surface fit as described below. Alternatively, if there are a large number of intensity signals (data points) that lie between these thresholds, or if a user selects this option, such as by selecting it through the user interface, a representative sample of the total number of signal intensity data points lying between the thresholds may be used to calculate the secondary surface. For example, a window may be used to select every $x^{th}$ intensity value (where x is a predetermined positive integer value) as the window moves over the surface of the array image, in a manner as described in more detail in application Ser. No. 10/859,868, so as to give a representative sample over all locations on the array. Further alternatively, a user-determined percentage of intensity values may be randomly filtered out to leave the representative sample for calculating the secondary surface. This percentage may be as high as 90, for example (thus leaving 10% or less of the number of features to be used for the fit).

At event 612, a secondary surface fit (secondary spatial fit) is calculated, using the intensity values from all features which, when those intensity values have the calculated offset values from the corresponding locations on the preliminary surface fit subtracted (i.e., filtered features), lie within the threshold surfaces 902$u$, 902$l$. To calculate the secondary surface, the full intensity values of those features (i.e., not the values having the preliminary offset subtracted) are used. The secondary surface fit may be calculated using any of the algorithms described above with regard to the preliminary surface fit. Typically, the Loess algorithm is used to calculate this surface.

The general equation for a surface is given by:

$$O(x,y) = p_1 x + p_2 y + p_3 \quad (3)$$

where $p_1$, $p_2$, and $p_3$ are coefficients determined for each feature coordinate (x, y). The following discussion provides a general mathematical description of the Loess method with accompanying figures. For each feature, the constants $p_1$, $p_2$, and $p_3$ are determined by minimizing the locally-weighted, least-squares error given by:

$$E(p_1, p_2, p_3) = \sum_{i=1}^{M} w_i (O_i - I_i)^2 \quad (4)$$

where $O_i = O(x_i, y_i)$;
$w_i$=the weighting function;
M=total number of neighboring filtered feature signal intensities (which have not had the offset values from the preliminary surface subtracted therefrom);

N=total number of filtered feature signal intensities considered for the surface calculation (which have not had the offset values from the preliminary surface subtracted therefrom); and
M<N.

In general, for each feature, the Loess method utilizes a set of M nearest neighbor filtered features to fit a best-fit plane O(x, y). The number of neighboring filtered features associated with each feature is given by:

$$M = \operatorname{ceil}(qN) \quad (5)$$

where $$\frac{p+1}{N} \le q < 1;$$

p=the degree of the best-fit function; and
q=a user specified input referred to as the "neighborhood size."

Figure 14:
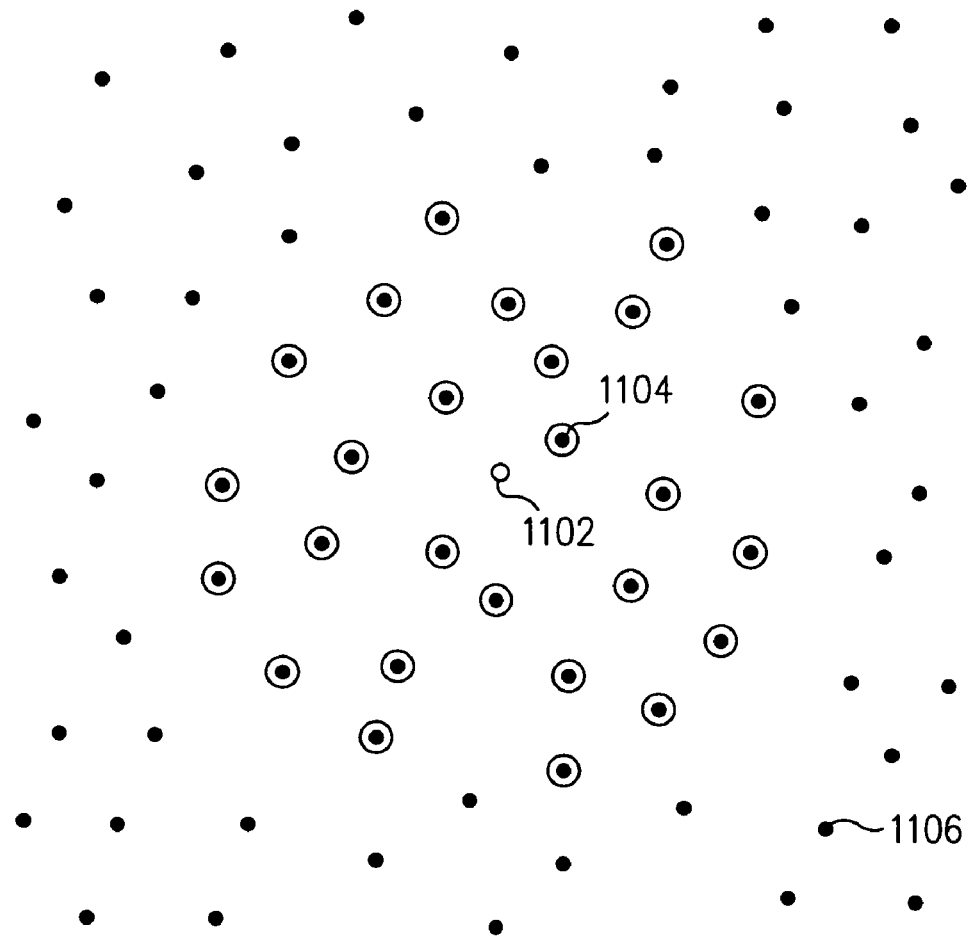
FIG. 14 illustrates a hypothetical set of neighboring filtered features.

Note that, for the best-fit plane O(x, y) given by equation (3), p is equal to "1." Typically, the neighborhood size q is selected somewhere in the range from about 0.20 to about 0.5 and represents the fraction of the total number of filtered features used to determine the best-fit plane O(x, y). FIG. 14 illustrates a hypothetical set of nearest-neighbor-filtered feature intensity values associated with currently considered feature 1102. In FIG. 14, the set of nearest neighbor filtered feature intensities are identified by circled filtered features, such as circled filtered feature 1104. Each filtered feature is assigned a weight according to its distance from the currently considered feature 1102. For example, in FIG. 14, the circled filtered features are assigned a weight $w_i$ according to their distances from currently considered feature 1102, and non-neighboring filtered features, such as filtered feature 1106, are assigned a weight of "0."

One of many possible weighting functions $w_i$ used for the Loess method is the "tricube" function given by:

$$w_i = w(u_i) = \begin{cases} (1 - u_i^3)^3 & \text{for } 0 \le u_i < 1 \\ 0 & \text{for } u_i > 1 \end{cases} \quad (6)$$

where $$u_i = \frac{\rho(x_i, y_i, x, y)}{d(x, y)}$$

is the normalized distance;
$\rho(x_i, y_i, x, y) = \sqrt{(x_i - x)^2 + (y_i - y)^2}$ is the distance, in intensity units, from the filtered feature to a neighboring filtered feature;
$d(x, y) = \sqrt{(x - x_m)^2 + (y - y_m)^2}$ is the distance from the feature to the farthest, neighboring filtered feature; and
$(x_m, y_m)$ is the farthest, neighboring filtered feature.

Figure 15A:
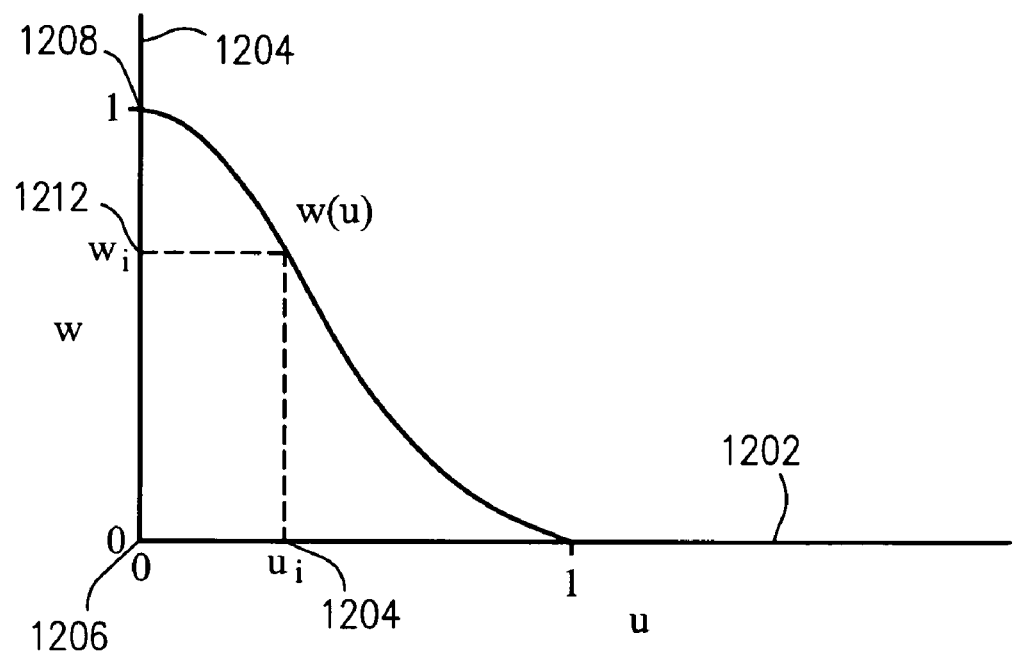
FIGS. 15A-15B illustrate a tri-cube weighting function w.
Figure 15B:
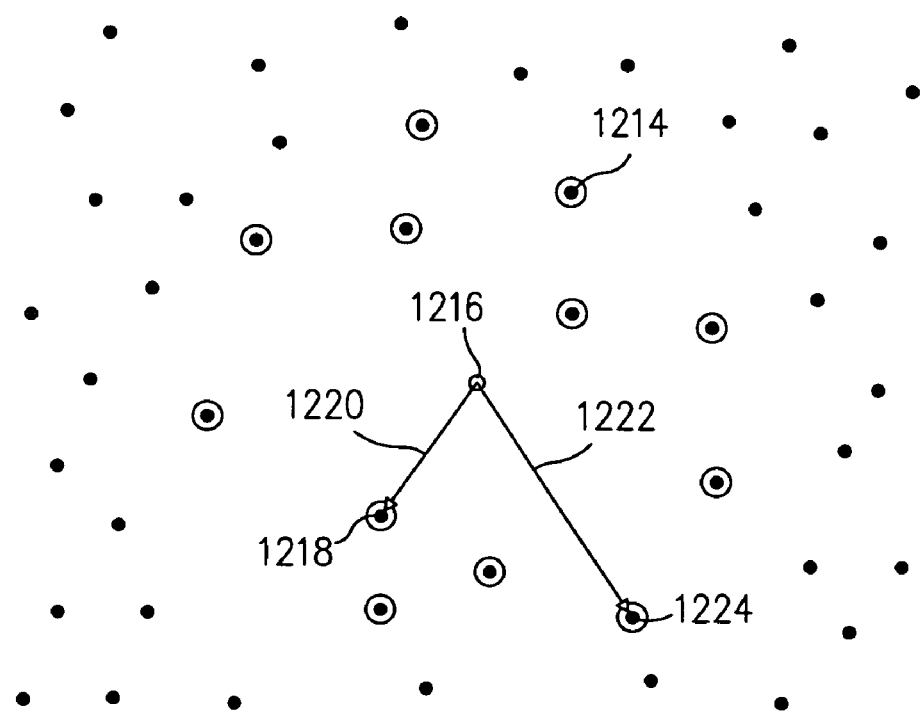

FIGS. 15A-15B illustrate the tricube weighting function w. In FIG. 15A, the tricube weighting function is plotted with respect to the horizontal axis 1202, corresponding to the normalized distance $u_i$, and the vertical axis 1204, corresponding to the weighting function values w ranging from "0" 1206 to "1" 1208. For example, a neighboring filtered feature having a normalized distance $u_i$ from the feature is assigned the weight value $w_i$ 1212. Neighboring filtered features are assigned a distance-dependent weight because filtered features that are closer to the feature are assumed to more closely approximate the feature intensity behavior at the feature rather than neighboring filtered features that are farther away.

FIG. 15B illustrates determination of the normalized distance $u_i$ given in equation (3). In FIG. 15B, the neighboring filtered features are identified by circled filtered features, such as circled filtered feature 1214. The normalized distance $u_i$ (1210 in FIG. 15A) from the considered feature 1216 to the neighboring filtered feature 1218 is determined by calculating the distance $\rho(x_i,y_i,x,y)$ 1220 from the considered feature 1216 to the neighboring filtered feature 1218 divided by the distance $d(x,y)$ 1222 from the feature 1216 to the farthest neighboring filtered feature 1224.

The minimum of equation (4) occurs when the gradient of $E(p_1,p_2,p_3)$ equals the zero vector, and is determined as follows:

$$\nabla E(p_1, p_2, p_3) = 2\sum_{i=1}^{M} w_i(O_i - I_i)\nabla O_i = (0, 0, 0) \qquad (7)$$

Therefore, the problem of determining the constants $p_1$, $p_2$, and $p_3$ for each feature is reduced to solving a linear system of three equations, each with three unknown constants $p_1$, $p_2$, and $p_3$.

The best-fit surface S can be smoothed by repeatedly applying the locally-weighted, least-squares regression for each feature. Rather than using the intensities $I_i$ at the filtered features, the best-fit plane values $O_i$ are used, and the weight function is modified. The locally-weighted, least-squares error is given by:

$$E(p'_1, p'_2, p'_3) = \sum_{i=1}^{M} W_i(O'_i - O_i)^2 \qquad (8)$$

where $O'_i = O'(x_i,y_i) = p'_1 x_i + p'_2 y_i + p'_3$ is the new best-fit plane; and $$W_i = w_i \cdot g_i.$$

Figure 16:
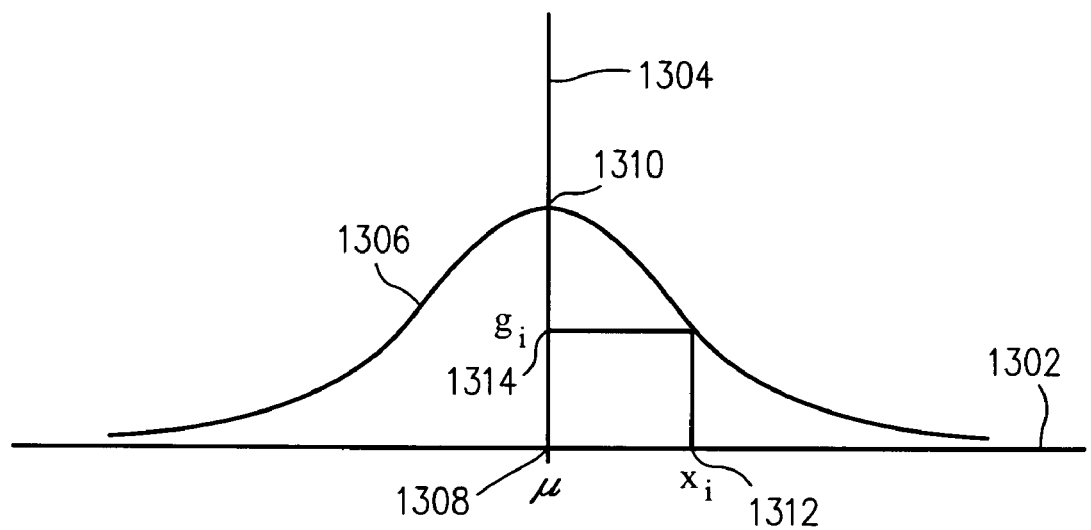
FIG. 16 illustrates a Gaussian weight distribution.

The updated weight function Wi is the product of the tricube weight function $w_i$ from equation (6) and a symmetric distribution function $g_i$. One of many possible symmetric distribution functions $g_i$ used to reduce the weight for filtered features is given by the Gaussian distribution:

$$g_i = g(x_i) = \frac{1}{\sigma\sqrt{2\pi}}\exp\left(-\frac{1}{2}\left(\frac{x_i - \mu}{\sigma}\right)^2\right) \qquad (9)$$

where $\mu$ and $\sigma$ are the mean and standard deviation, respectively, for the neighborhood of M filtered features i, and $x_i$ is the residual $(I_i-\mu)$. FIG. 16 illustrates a Gaussian weight distribution employed to account for large residuals. In FIG. 16, the horizontal axis 1302 corresponds to the intensity, the vertical axis 1304 corresponds to the normalized weighting function g, and the Gaussian distribution given in equation (9) is represented by the curve 1306. The Gaussian weighting values $g_i$ range from "0" 1308 to "1" 1310. A neighborhood filtered feature having a residual $x_i$ 1312 is assigned the weight value $g_i$ 1314.

After the entire set of L best-fit function surface intensity values $O_i$, are smoothed, the best-fit surface S is constructed by assembling the best-fit function intensity values $O_i$ to give the following:

$$S=\{(x_i,y_i),O_i,C\}_{i=1}^{L} \qquad (10)$$

Further details about the locally weighted (Loess) method described above can be obtained from Cleveland, W. S. (1979) "Robust Locally Weighted Regression and Smoothing Scatterplots," *Journal of the American Statistical Association*, Vol. 74, pp. 829-836, and Cleveland, W. S., and Devlin, S. J. (1988) "Locally Weighted Regression: An Approach to Regression Analysis by Local Fitting," *Journal of the American Statistical Association*, Vol. 83, pp. 596-610, both of which are incorporated herein, in their entireties, by reference thereto.

If there are a large number of intensity signals (data points) to be processed for the secondary fitting calculation, or, generally, in order to speed up processing, and/or if a user selects this option, such as by selecting it through the user interface, a representative sample of the total number of signal intensity data points may be used to calculate the secondary surface. For example, a window may be used to select every $x^{th}$ intensity value (where x is a predetermined positive integer value) as the window moves over the surface of the array image, in a manner as described in more detail in application Ser. No. 10/859,868, so as to give a representative sample over all locations on the array. Further alternatively, a user-determined percentage of intensity values may be randomly filtered out to leave the representative sample for calculating the secondary surface.

Figure 17:
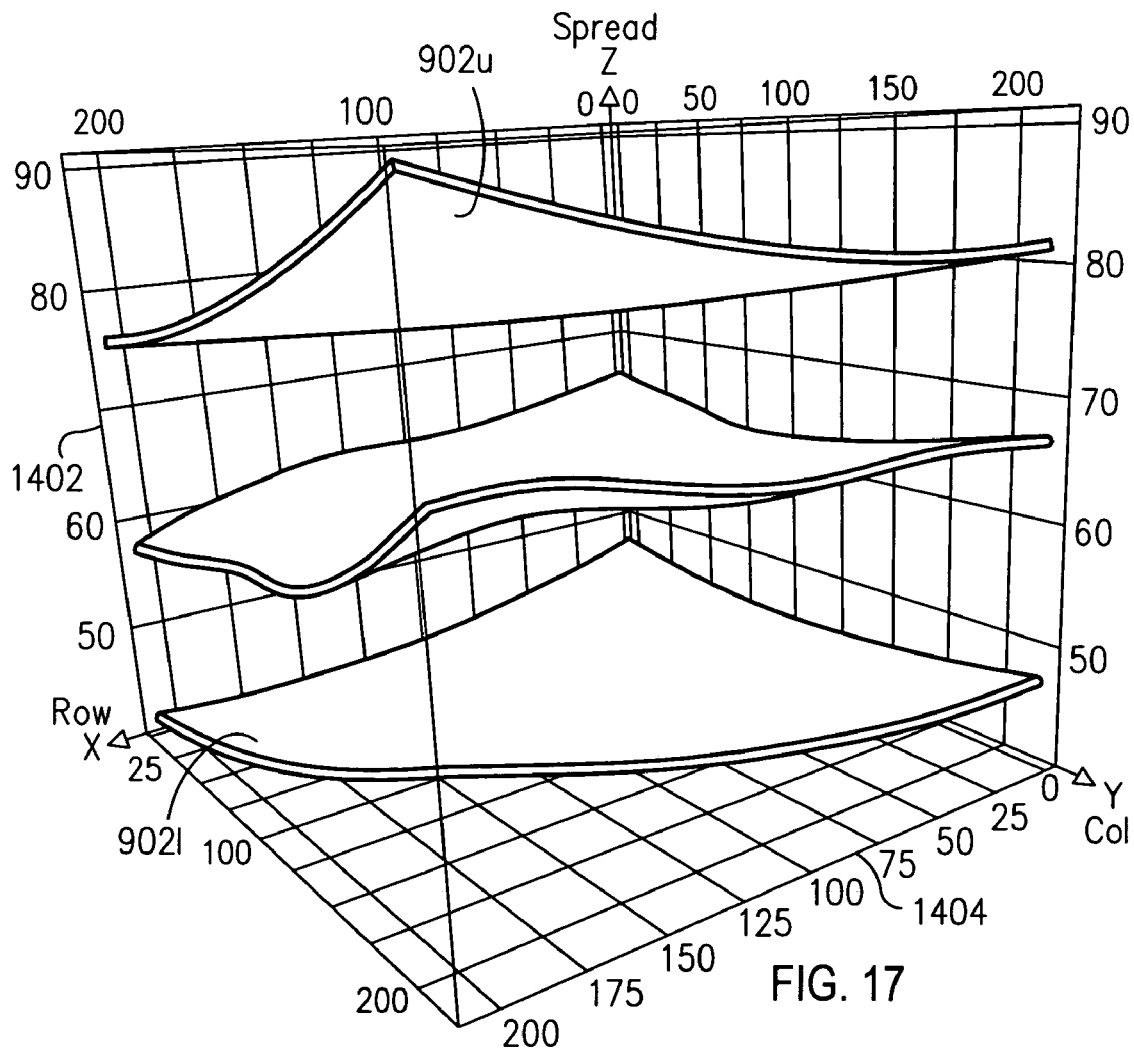
FIG. 17 illustrates a surface 1402 representing a hypothetical best-fit surface calculated from the data points that were found between the upper and lower threshold surfaces shown in FIG. 12.

The data points of a best-fit surface S characterizes the spatial-intensity trends for a channel of the chemical data set. FIG. 17 illustrates a surface 1402 representing a hypothetical best-fit surface calculated from the data points that were found between the upper 902u and lower 902l threshold surfaces described with regard to FIG. 12. It can be observed that this surface 1402 is differently shaped than surfaces 900, 902u and 902l and is somewhat offset from the previous "zero" values identified by the preliminary surface fit 902, owing to the contribution of the signal intensities from features that are not negative controls and that fell within the upper and lower thresholds.

As with the preliminary surface fit, the surface values on surface 1402 are calculated for the corresponding locations of all features whose signal intensities were not used in calculating the secondary surface fit. This can be seen on the resulting surface 1402 which has surface values corresponding to all locations across the array, which is mapped by the grid 1404. Once the surface 1402, including the calculated values has been calculated, at event 614 (FIG. 8) the intensity values of each feature on the array are corrected for offset bias by subtracting the value on the surface 1402 at a location corresponding to the location of the feature being corrected, from the intensity value of the feature. At event 616 the process checks to see if there are any remaining subsets (channels) of data to be processed. If there is another channel of data points to process, the processing returns to event 606. If, at event 616, it is found that all channels have been processed, the flow control returns or resets to the beginning of the process, ready for initiation of any further processing as directed by the user interface.

Figure 18:
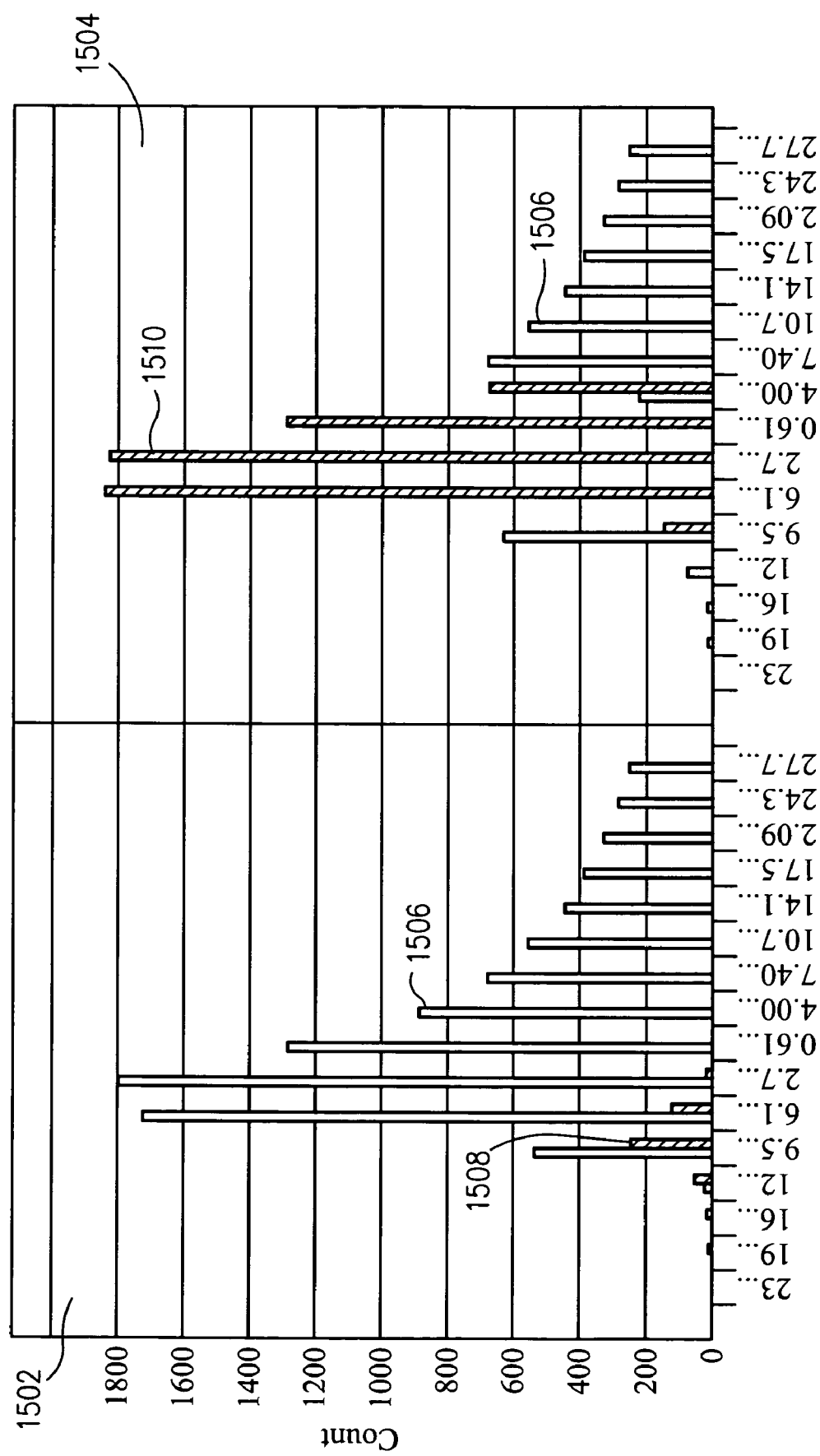
FIG. 18 illustrates histograms showing improved background estimation results from present techniques described herein, versus an earlier technique.

FIG. 18 illustrates improved results from the present techniques, versus an earlier technique mentioned above with regard to FIG. 2. FIG. 18 shows histograms 1502 and 1504 each plotting all feature signals from a chemical array (light bars) by intensity along the X-axis, versus "Count" or number of features at those signal intensities. The signal plotted is after the first negative control fit subtraction (event 608 of FIG. 8). The bars 1508 in histogram 1502 represent the lowest one percent of the signal intensities that were selected in order to estimate offset according to the technique mentioned above with regard to FIG. 2. The bars 1510 in histogram 1504 represent the signal intensities of the features that lie within the signal intensity range of the negative control spread range (after event 610 in FIG. 8). This feature set will include both negative control features and non-control features. Note that the histograms of FIG. 18 are zoomed in and do not show some of the high signal features off scale to the right. The true value of "zero" intensity is most likely to be around the mode of the histogram plot of all feature intensities (i.e., the mode of all the bars 1502 and 1504). By comparing the bars 1508 and 1510 to the all the bars 1502 or 1504, it can be readily observed that bars 1510 approximate the mode of the distribution much more closely than bars 1508 and thus, that the approximation based on selecting the lowest 1% of the signal intensities substantially underestimated the true value of "zero" signal intensity. It can be observed that the center of bars 1508 is about −10 counts, rather than the ideal zero counts. Of course, a different target could produce different erroneous results using the prior method of FIG. 2. For example, the method that uses the lowest 1% of feature intensity signals could result in an over subtraction of the background.

Figure 2:
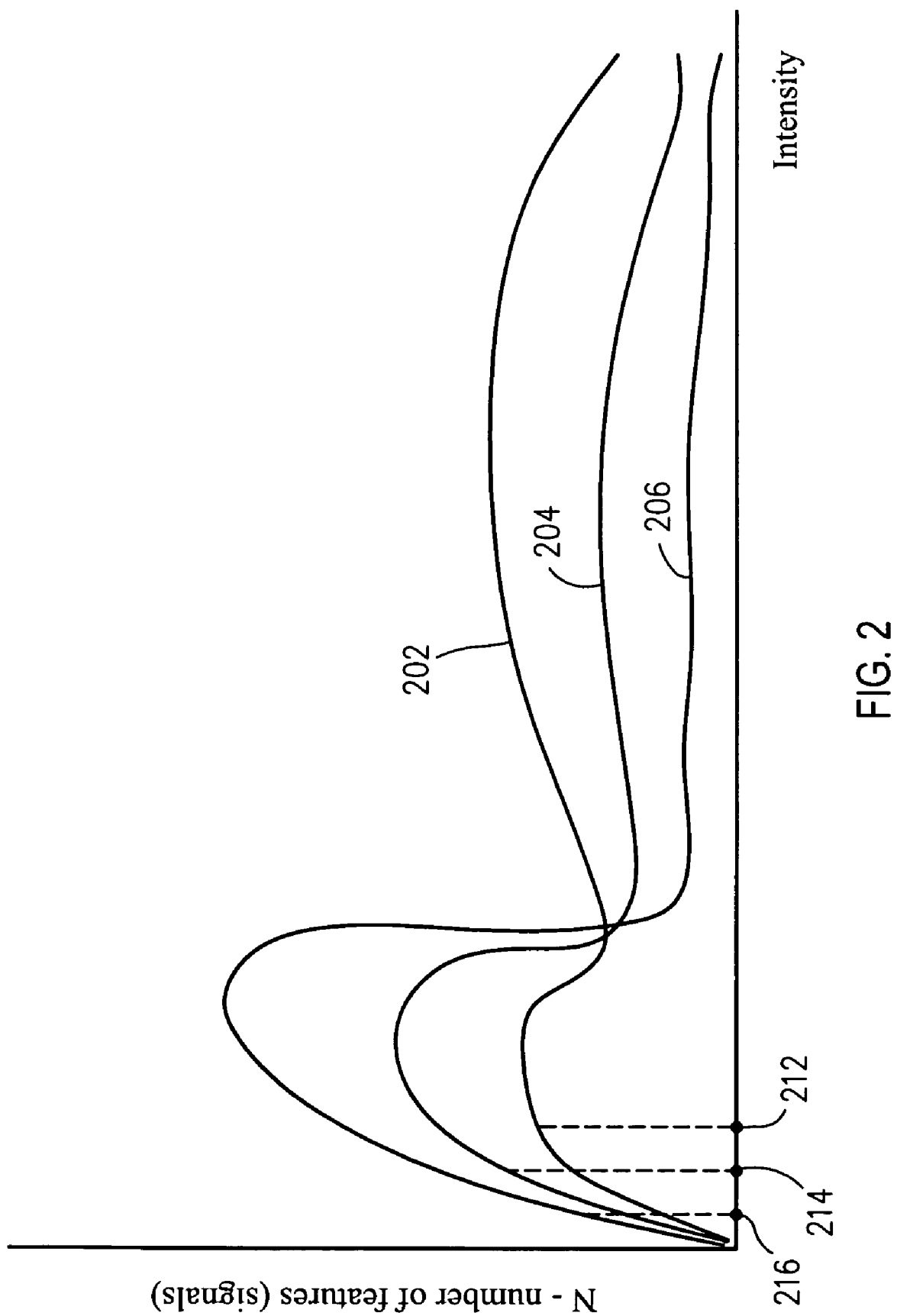
FIG. 2 illustrates three histograms plotted to represent the signal data from three hypothetical chemical arrays.
Figure 19:
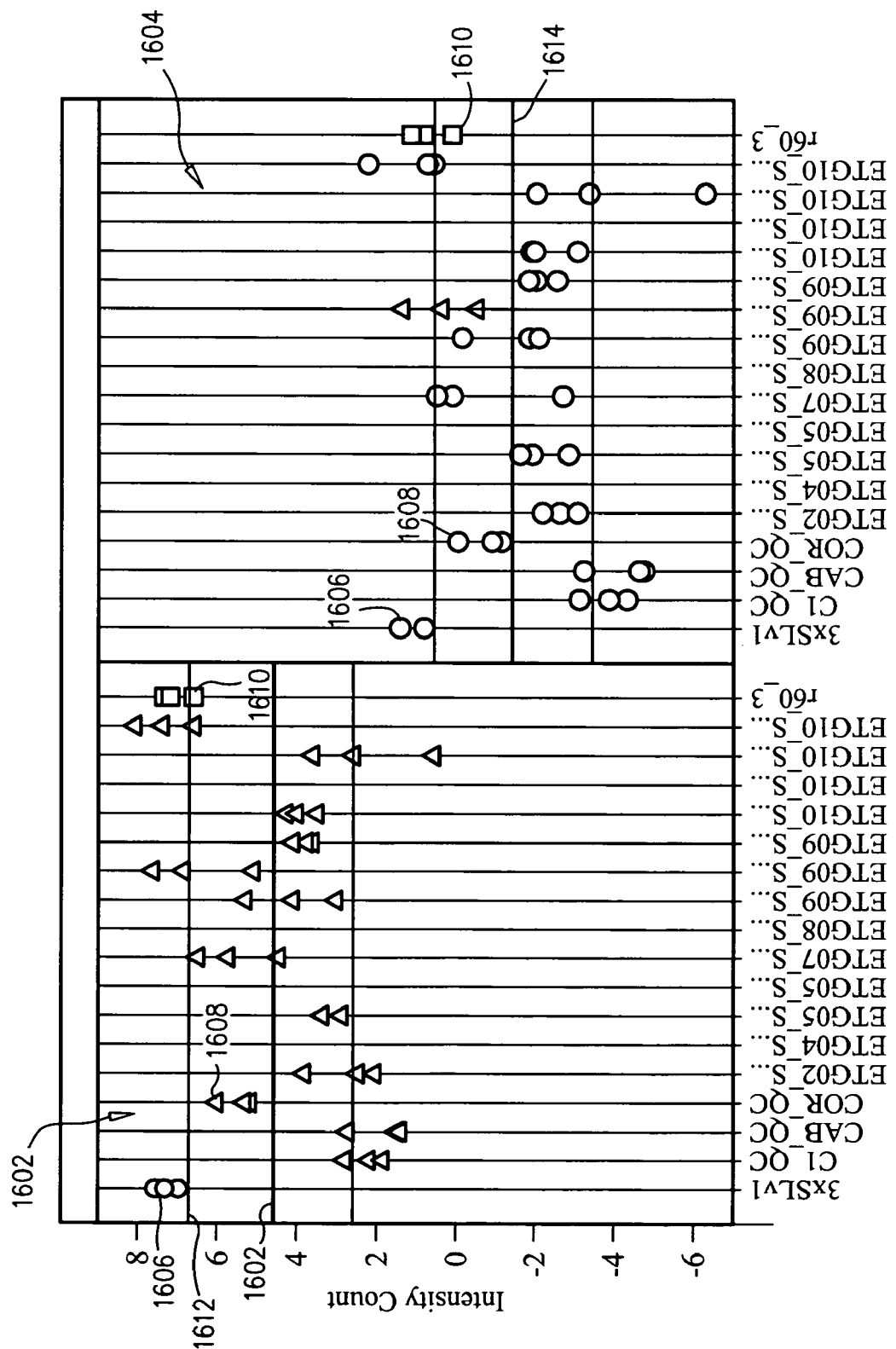
FIG. 19 shows plots of intensity counts of three different types of negative control probes after background offset correction according to an offset correction technique according to the present invention, compared to another technique.

FIG. 19 shows plots 1602 and 1604 of intensity counts of three different types of negative control probes (signals 1606, 1608, 1610) after offset correction according to a technique referred to with regard to FIG. 2 above (as shown in plot 1602) and according to the present methods as shown in plot 1604. Features 1606 are from negative control features of the type commonly referred to as "hairpins" After subtracting the calculated background offset signal, these negative control signals should be around zero intensity. Using the method described in FIG. 2 above, where the lowest 1% of signal intensities were selected for surface fitting and estimation of the offset, it can be seen that the hairpin signals 1606 still register nearly 8 counts of intensity, whereas using the present approach, the hairpin signals are shown down at around 1 or less than one count. The negative control probes from which signals 1608 were generated contain bacterial sequences, and the sample that was applied to the array was a human sample, so the bacterial sequences were expected not to bind with the sample. The negative control probes from which signal 1610 were generated were sequences that were designed with bioinformatics techniques so as not to match any sequences in the human genome, and these designed sequences were tested empirically with many human targets. In each of these cases, it can be observed that the present techniques more accurately subtracted the background offset signals from all of the types of negative control signals, as shown by the closer approximation to zero in the results plotted in plot 1604, relative to those shown in plot 1602. The average, background-subtracted signal of all three types of negative controls in plot 1602 is shown by the horizontal bar 1612 at around 5 counts, while that for plot 1604 (see 1614) is around −1 counts. Although the estimate for zero according to the present techniques is not exactly at zero, it is substantially closer than the prior approach to which it has been compared. Further, there is always some statistical deviation or spread around any signal reading, including a reading of what is considered zero. Plots 1602 and 1604 also show two lines around the average signal that correspond to the average ± one standard deviation of the average signal. It can be observed from plot 1604 that the "zero" level lies within one standard deviation of the average calculated background-subtracted signal.

Figure 20:
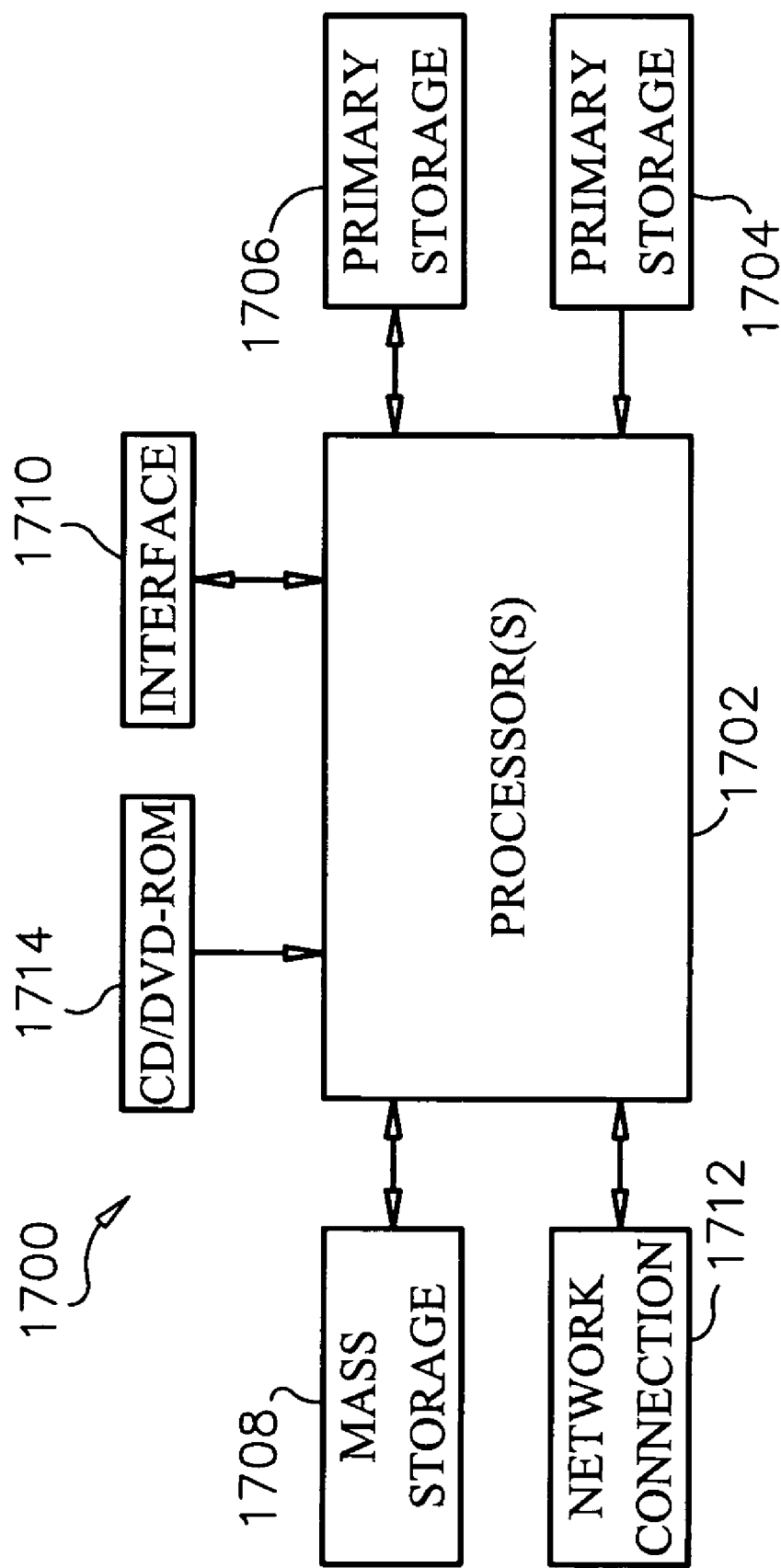
FIG. 20 is a schematic illustration of a typical computer system that may be used to perform procedures described herein.

FIG. 20 is a schematic illustration of a typical computer system that may be used to perform procedures described above. The computer system 1700 includes any number of processors 1702 (also referred to as central processing units, or CPUs) that are coupled to storage devices including primary storage 1706 (typically a random access memory, or RAM), primary storage 1704 (typically a read only memory, or ROM). As is well known in the art, primary storage 1704 acts to transfer data and instructions uni-directionally to the CPU and primary storage 1706 is used typically to transfer data and instructions in a bi-directional manner Both of these primary storage devices may include any suitable computer-readable media such as those described above. A mass storage device 1708 is also coupled bi-directionally to CPU 1702 and provides additional data storage capacity and may include any of the computer-readable media described above. Mass storage device 1708 may be used to store programs, data and the like and is typically a secondary storage medium such as a hard disk that is slower than primary storage. It will be appreciated that the information retained within the mass storage device 1708, may, in appropriate cases, be incorporated in standard fashion as part of primary storage 1706 as virtual memory. A specific mass storage device such as a CD-ROM or DVD-ROM 1714 may also pass data uni-directionally to the CPU.

CPU 1702 is also coupled to an interface 1710 that includes one or more input/output devices such as video monitors, printers, scanners or other readers, track balls, mice, keyboards, microphones, touch-sensitive displays, transducer card readers, magnetic or paper tape readers, tablets, styluses, voice or handwriting recognizers, or other well-known input devices such as, of course, other computers. Plots such as those described and shown herein may be outputted to one or much such output devices for human observation and use. Additionally, or alternatively, numeric corrected signal readings may be outputted to a user via one or more of such output devices and/or transmitted to another computer or device for observation and use by another user. Finally, CPU 1702 optionally may be coupled to a computer or telecommunications network using a network connection as shown generally at 1712. With such a network connection, it is contemplated that the CPU might receive information from the network, or might output information to the network in the course of performing the above-described method steps. The above-described devices and materials will be familiar to those of skill in the computer hardware and software arts.

The hardware elements described above may implement the instructions of multiple software modules for performing the operations of this invention. For example, instructions for calculating statistical significance may be stored on mass storage device 1708 or 1714 and executed on CPU 1708 in conjunction with primary memory 1706.

In addition, embodiments of the present invention further relate to computer readable media or computer program products that include program instructions and/or data (including data structures) for performing various computer-implemented operations. The media and program instructions may be those specially designed and constructed for the purposes of the present invention, or they may be of the kind well known and available to those having skill in the computer software arts. Examples of computer-readable media include, but are not limited to, magnetic media such as hard disks, floppy disks, and magnetic tape; optical media such as CD-ROM, CDRW, DVD-ROM, or DVD-RW disks; magneto-optical media such as floptical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A method for quantifying and removing offset bias signals in a chemical array data set having one or more channels, said method comprising:
for each channel of data in the chemical array data set, and using at least one computer processor,
selecting a first set of features from the data set;
calculating surface intensities for each feature in the first selected set of features;
calculating a spread of the intensity values of the first selected set of features from the calculated surface intensities;
selecting a second set of features the intensity values of which are within a range of intensity values between ± spread times a predetermined multiplier;
calculating surface intensities for features in the second selected set of features;
calculating surface intensities for all other features in the data set for the channel from the calculated surface intensities for each feature in the second selected set;
correcting feature intensities of the channel features by subtracting the surface intensities for each feature in the second selected set at locations that correspond to respective locations of said feature intensities; and
outputting the corrected feature intensities.

2. The method of claim 1, wherein the selected features in said first set are negative control features.

3. The method of claim 1, wherein said second set includes said first set.

4. The method of claim 1, wherein surface intensities are calculated for all features in the second selected set.

5. The method of claim 1, further comprising sampling the second selected set of features, wherein said calculating surface intensities is performed on a sampled, subset of said second selected set that is smaller than said second selected set.

6. The method of claim 5, wherein said sampling is performed with a moving window filter.

7. The method of claim 1, further comprising randomly selecting a predetermined percentage of features from the second selected set of features, wherein said calculating surface intensities is performed on the signal intensities of the randomly selected features, and wherein said predetermined percentage is less than one hundred percent.

8. The method of claim 1, wherein at least one of said selecting steps further includes excluding features having non-uniform intensity distributions.

9. The method of claim 1, wherein said calculating surface intensities for each feature in the first selected set of features comprises calculating a surface fit to intensity values of said features with a polynomial approximation algorithm.

10. The method of claim 9, wherein said polynomial approximation algorithm is a second-order polynomial approximation algorithm.

11. The method of claim 1, wherein said calculating surface intensities for each feature in the first selected set of features comprises locally-weighted, least-squares regression.

12. The method of claim 1, wherein said calculating surface intensities for features in the second selected set of features comprises locally-weighted, least-squares regression.

13. The method of claim 1, wherein said calculating surface intensities for features in the second selected set of features comprises calculating a surface fit to intensity values of said features with a polynomial approximation algorithm.

14. The method of claim 13, wherein said polynomial approximation algorithm is a second-order polynomial approximation algorithm.

15. A method for quantifying and removing offset bias signals in a chemical array data set having one or more channels, said method comprising:
for each channel of data in the chemical array data set, and using at least one computer processor,
selecting a first set of features from the data set;
calculating surface intensities for features in the first selected set of features and calculating surface intensities of features not in the first selected set, from said calculated surface intensities for features in the first selected set of features;
selecting a second set of features the intensity values of which are within a range of correspondingly located surface intensity values defined by upper and lower threshold intensities;
calculating secondary surface intensities for features in the second selected set of features and calculating secondary surface intensities for all other locations on the array that were not locations corresponding to the features having secondary surface intensities calculated therefore;
correcting feature intensities of the channel features as a function of said secondary surface intensities; and
outputting the corrected feature intensities.

16. The method of claim 15, wherein said upper and lower threshold intensities are calculated as a function of said calculated surface intensities.

17. The method of claim 16, wherein said function of said calculated surface intensities includes calculation of a spread of the intensity values of the selected set of features from the calculated surface intensities.

18. The method of claim 17, wherein the spread is calculated by a robust technique, excluding outliers of the intensity values.

19. The method of claim 15, wherein said correcting feature intensities comprises subtracting secondary surface intensities at locations that correspond to respective locations of said feature intensities.

20. A system for quantifying and removing offset bias signals in a chemical array data set having one or more channels, said system comprising:
at least one computer processor;
an interface through which one or more chemical array data sets are received by the system; and
a program, stored in one or more memory components and executed by at least one computer processor that, for each channel, selects a first set of features from the data set; calculates surface intensities for each feature in the first selected set of features and calculates surface intensities of features not in the first selected set, from said calculated surface intensities for features in the first selected set of features; selects a second set of features the intensity values of which are within a range of correspondingly located surface intensity values defined by upper and lower threshold intensities; calculates secondary surface intensities for features in the second selected set of features and calculates secondary surface intensities for all other locations on the array that were not locations corresponding to the features having secondary surface intensities calculated therefore; and corrects feature intensities of the channel features as a function of said secondary surface intensities.

21. A non-transitory computer-readable media having instructions stored thereon that, when executed by a processor, cause the processor to perform the method of claim 1.

22. A non-transitory computer-readable media having instructions stored thereon that, when executed by a processor, cause the processor to perform the method of claim 15.

* * * * *

UNITED STATES PATENT AND TRADEMARK OFFICE
CERTIFICATE OF CORRECTION

PATENT NO. : 7,881,876 B2
APPLICATION NO. : 11/580744
DATED : February 1, 2011
INVENTOR(S) : Christian A. Le Cocq et al.

It is certified that error appears in the above-identified patent and that said Letters Patent is hereby corrected as shown below:

On the Title page, in Item (56), under "Other Publications", in column 2, line 6, delete "2004." and insert -- 2004.) --, therefor.

On the Title page, in Item (57), under "Abstract", in column 2, line 7, delete "intensifies" and insert -- intensities --, therefor.

On the Title page, in Item (57), under "Abstract", in column 2, line 12, delete "intensifies" and insert -- intensities --, therefor.

Signed and Sealed this
Twenty-first Day of June, 2011

David J. Kappos
*Director of the United States Patent and Trademark Office*